US007158692B2

(12) United States Patent
Chalana et al.

(10) Patent No.: US 7,158,692 B2
(45) Date of Patent: Jan. 2, 2007

(54) SYSTEM AND METHOD FOR MINING QUANTITIVE INFORMATION FROM MEDICAL IMAGES

(75) Inventors: Vikram Chalana, Mill Creek, WA (US); Stephen Fogarasi, Everett, WA (US); Lydia Ng, Seattle, WA (US); John Oelund, Redmond, WA (US); Sayan Pathak, Seattle, WA (US); Steven Racki, Ottawa (CA); Bobbi Sparks, Mountlake Ter., WA (US); Bradley Wyman, Kirkland, WA (US)

(73) Assignee: Insightful Corporation, Seattle, WA (US)

( * ) Notice: Subject to any disclaimer, the term of this patent is extended or adjusted under 35 U.S.C. 154(b) by 534 days.

(21) Appl. No.: 10/271,916

(22) Filed: Oct. 15, 2002

(65) Prior Publication Data

US 2003/0174872 A1   Sep. 18, 2003

Related U.S. Application Data

(60) Provisional application No. 60/329,843, filed on Oct. 15, 2001, provisional application No. 60/329,827, filed on Oct. 15, 2001.

(51) Int. Cl.
*G06K 9/32* (2006.01)
*G06K 9/00* (2006.01)

(52) U.S. Cl. ......................... 382/294; 382/128; 382/173
(58) Field of Classification Search ............... 382/173, 382/289, 305, 190, 181, 128–134, 294; 600/410; 707/104
See application file for complete search history.

(56) References Cited

U.S. PATENT DOCUMENTS 5,970,499 A * 10/1999 Smith et al. ............. 707/104.1
6,430,430 B1 * 8/2002 Gosche ....................... 600/410

* cited by examiner

*Primary Examiner*—Kanjibhai Patel
(74) *Attorney, Agent, or Firm*—DLA Piper US LLP

(57) ABSTRACT

A system for image registration and quantitative feature extraction for multiple image sets. The system includes an imaging workstation having a data processor and memory in communication with a database server in communication. The a data processor capable of inputting and outputting data and instructions to peripheral devices and operating pursuant to a software product and accepts instructions from a graphical user interface capable of interfacing with and navigating the imaging software product. The imaging software product is capable of instructing the data processor, to register images, segment images and to extract features from images and provide instructions to store and retrieve one or more registered images, segmented images, quantitative image features and quantitative image data and from the database server.

47 Claims, 28 Drawing Sheets

SYSTEM AND METHOD FOR MINING QUANTITIVE INFORMATION FROM MEDICAL IMAGES

CROSS REFERENCE TO RELATED APPLICATIONS

This application claims priority under 35 U.S.C. § 119(e) to provisional application No. 60/329,843, filed Oct. 15, 2001, entitled "METHOD AND SYSTEM FOR MINING QUANTITIVE INIFORMATON FROM MEDICAL IMAGES", which is hereby fully incorporated by reference and provisional application No. 60/329,827, filed Oct. 15, 2001, entitled "Method and System for Image Analysis and Syntactic Searches", which is hereby fully incorporated by reference.

FIELD OF INVENTION

This invention is directed to the field of medical imaging in general and particularly is directed towards the use of medical imaging in clinical diagnosis, clinical trials and clinical research, including drug discovery and clinical trials of drugs and more particularly focuses on quantitative information extraction from medical images from one or more modalities, tracking of this information over time, and archiving and mining of this information.

BACKGROUND OF THE INVENTION

Extraction of quantitative anatomical information from three-dimensional medical images and persistent storage and retrieval of this information has many applications in clinical diagnosis, drug development, and clinical research. As imaging devices, such as Magnetic Resonance (MR), computed tomography (CT), positron emission tomography (PET), and ultrasound, continue to improve in resolution and contrast, they are increasingly being used for these applications.

In clinical applications, the size and shape of an anatomical structure and its changes in size and shape over time inferred from medical images is often used an indicator of a disease condition. For instance, lesion size and its growth measured on CT images is indicative of cancer, a rapid enlargement of the prostate measured from ultrasound images is indicative of prostate cancer, and the shrinking of the hippocampus measured from MR images is associated with the onset of Alzheimer's Disease.

In all phases of drug development—drug discovery, animal studies, and pre-clinical and clinical trials—medical images are being increasingly used to study disease progression and to test the efficacy of a drug. Once again the goal is to measure the shapes and sizes and the changes in the shapes and sizes of anatomical and pathological structures for a large collection of patient image data. For example, the efficacy of a drug to treat multiple sclerosis is measured by the reduction in the sizes of the MS lesions on MR images of the brain.

The conventional practice is to extract size and shape information from images in most of these applications using either rough estimation based on appearance or painstaking manual outlining of anatomy or pathology on sequences of images. Both these currently practiced methods suffer from lack of accuracy and precision (due to inter-observer variability.) In addition, the latter method has a severe disadvantage in terms of the cost and time taken to extract size and shape information. Moreover, manual tracking of shapes and sizes in serial data is extremely difficult to do manually.

The conventional methods are deficient in that they do not allow the combination of various segmentation methods, registration methods, feature extraction methods, and database storage and retrieval. The conventional methods are further deficient in that features that have been extracted cannot be saved back into the database, linked, quantified and queried upon. Based upon these deficiencies alone none of these systems can perform a dual purpose as an image extracting and image mining system. Conventionally, two separate systems are employed that are not accessible or linked to each other concurrently.

In clinical practice there is also a need for the ability to register and quantitatively measure and compare lesions or tissues. A patient may undergo multiple scans at different time points to monitor disease or treatment progression. A system which can register these images and measure and compare disease progress can aid in the proper treatment planning of this patient.

The prior art is also deficient in that prior art systems do not allow quantitative tracking of shapes and sizes of anatomy or pathology over time. Furthermore, the prior art systems are deficient in that they do not provide a fast, automatic, multimodal registration method or process.

Several commercial medical imaging viewing stations are available which allow users to view images that are archived on a database. A review of these systems will emphasis their shortcomings. Some examples are PACS systems sold by GE, Marconi, Voxar, and Vital Images. All of these systems provide basic 2D and 3D image viewing capabilities and have databases attached to them that store the images and the patient data. Some of these products even provide some basic interactive segmentation and feature extraction methods. The GE system, for instance, even provides a registration method for multi-modality fusion.

However, all these systems are designed to handle individual patient data and therefore the reports generated are single patient oriented. All these systems use the database as nothing more than an image archive. The quantitative features extracted are not stored in the database so that they fail to link and quantify the data and do not support the mining of quantitative information. Moreover, none of these systems support tracking of serial/longitudinal data. Nor do the prior art systems provide multi-channel tissue classification or shape-based interpolation. There are several conventional systems that provide segmentation, registration, and visualization tools, for instance Analyze from the Mayo Clinic and 3D Viewnix from the University of Pennsylvania, just to name a few. These systems do not provide any level of database or image mining support.

It is desirable to provide a system that provides multi-channel tissue classification, region growing, interactive tracing for precise delineation of structure boundaries and shape-based interpolation utilizing semi-automatic tools for extraction and tracking of quantitative information from 2D or 3D medical images. It is also desirable to provide a system that provides the ability to view 2D or 3D medical images in various ways, fuse information from one or more imaging modalities, store and archive this information in a database, and discover patterns and trends in the data by mining this information and it is these ends that the present invention is directed.

SUMMARY OF THE INVENTION

The present invention comprises an Imaging System for quantitative information extraction from multi-modal medical images such as CT, MR, ultrasound and PET, for tracking of this information over time, and for archiving and mining of this information that overcome the deficiencies of the prior art. Furthermore, the system uniquely combines various image segmentation methods, image registration methods, image feature extraction methods, audit trail recording, and database storage and retrieval methods and routines into seamless environment capable of enhancing clinical diagnosis and research.

The present invention has been made in view of the above circumstances and has as an aspect a system for multi-modality image registration and quantitative feature extraction for multiple patients and/or multiple time points, wherein all phases of the registration, segmentation and quantitative feature extraction can be performed concurrently.

A further aspect of the present invention can be characterized as several methods for segmenting or identifying regions of interest within the image. The methods for segmenting include 2D and 3D seedfill, multi-channel segmentation, live-wire contouring, snakes, manual tools and combinations of these tools.

Additional aspects and advantages of the invention will be set forth in part in the description which follows, and in part will be obvious from the description, or may be learned by practice of the invention. The aspects and advantages of the invention will be realized and attained by means of the elements and combinations particularly pointed out in the appended claims.

To achieve these and other advantages and in accordance with the purpose of the present invention, as embodied and broadly described, the present invention can be characterized according to one aspect of the present invention as a system for multi-modality image registration and quantitative feature extraction for multiple patients or one patient at multiple time points. The system includes an imaging workstation having a data processor and memory in communication with a database server. The data processor capable of inputting and outputting data and instructions to peripheral devices and operating pursuant to a software product and accepts instructions from a graphical user interface capable of interfacing with and navigating the imaging software product. The imaging software product is capable of instructing the data processor, to register images, segment images and to extract features from images and provide instructions to store and retrieve one or more registered images, segmented images, quantitative image features and quantitative image data and from the database server and to record an audit trail of significant user interactions with the system.

It is to be understood that both the foregoing general description and the following detailed description are exemplary and explanatory only are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
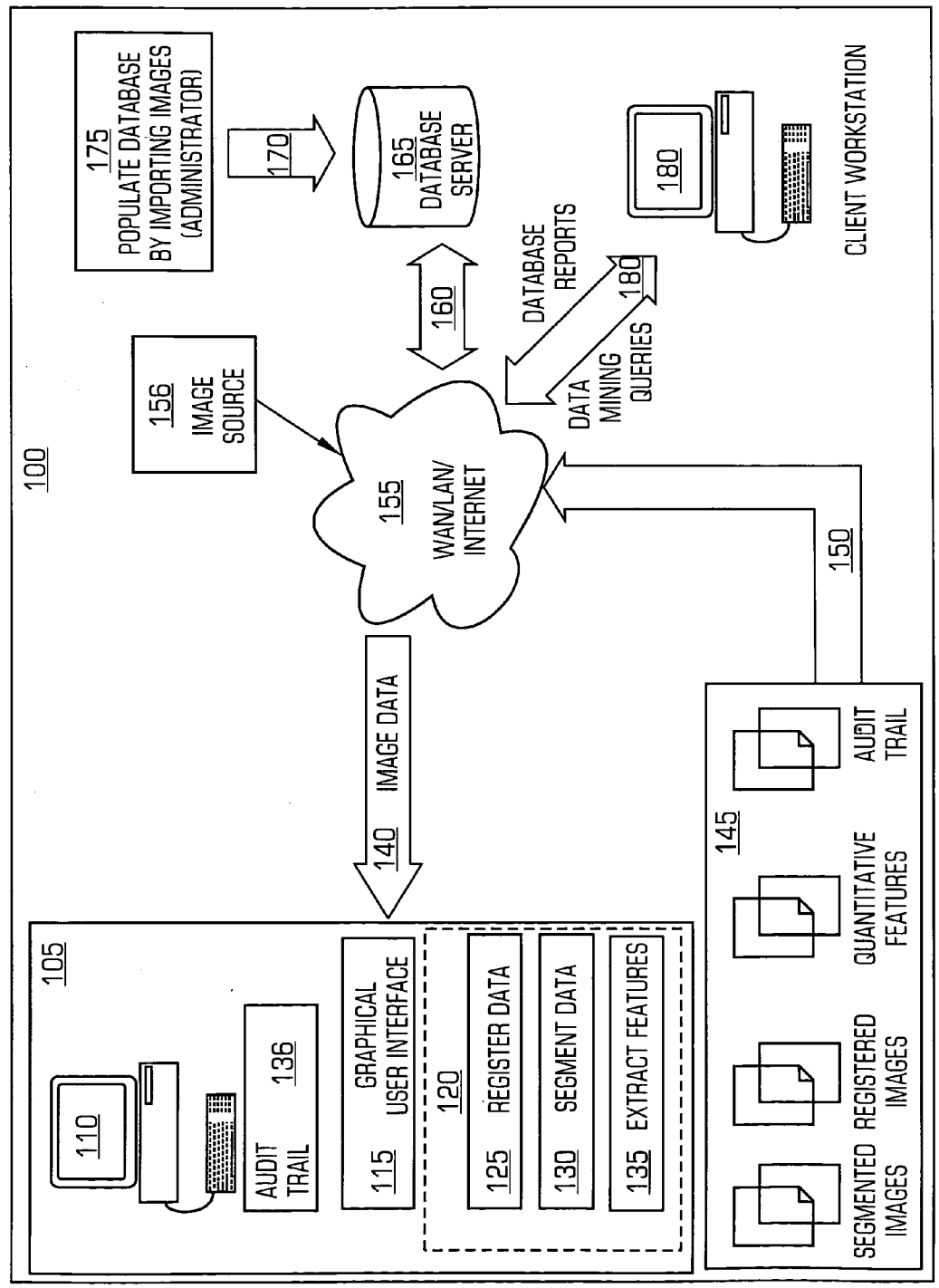
FIG. 1 depicts a schematic diagram of the imaging system architecture of the present invention.

Reference will now be made in detail to the present embodiments of the invention, examples of which are illustrated in the accompanying drawings. Wherever possible, the same reference numbers will be used throughout the drawings to refer to the same or like parts (elements).

In accordance with the invention, the present invention can be characterized according to one aspect of the present invention as a system for multi-modality image registration and quantitative feature extraction for multiple patients. The system includes an imaging workstation having a data processor and memory in communication with a database server. The data processor is capable of inputting and outputting data and instructions to peripheral devices and operating pursuant to a software product and accepts instructions from a graphical user interface capable of interfacing with and navigating the imaging software product. The instructions may also be stored and executed from a batch file. The imaging software product is capable of instructing the data processor, to register images, segment images and to extract features from images and provide instructions to store and retrieve one or more registered images, segmented images, quantitative image features, quantitative image data and audit trail information from the database server.

Embodiments of the present invention provide improved methods and systems for facilitating the registration, segmentation and quantitative feature extraction retrieval and storage of images and image sets. This invention can be used for analyzing a single set of images or comparing sets of images as might be generated by repeated scans over time of a patient or multiple scans and patients in a clinical trial. Without limiting the scope of the invention the embodiment of the invention will be described in terms of a clinical trial. In all phases of drug development, from drug discovery to animal studies, and from pre-clinical to late-phase clinical trials, medical images are being increasingly used to study disease progression and to test the efficacy of new drugs. Quantitative features extracted from two-dimensional (2D) and three-dimensional (3D) medical images have been used as surrogate endpoints in clinical trials such as cancer, multiple sclerosis (MS), osteo-arthritis, and Alzheimer's disease. For example:

1) in clinical trials of cancer drugs, the tumor volume and the tumor cross-sectional diameter measured from MR or CT images have been used as endpoints;

2) in MS drug trials, the total lesion load (number of lesions and total lesion volume) measured from multi-echo MR images of the brain was employed;

3) for osteo-arthritis drugs, the cartilage thickness and cartilage volume measured from MR images of the knees was used to show effectiveness; and 4) for Alzheimer's disease, the total brain volume and total hippocampus volume measured from MR images of the brain is used as an indicator of disease progression.

To process such varied and large image data sets acquired during drug trials, clinical research trials, etc., a system and method for mining quantitative information from medical images (here-in-after the "Image Analysis System") capable of registering and segmenting medical images in three-dimensions is needed. The Image Analysis System of the present invention comprises a unique combination of an imaging workstation including imaging tools, such as, image segmentation methods, image registration methods, quantitative feature extraction tools, an integrated database management system and database, reporting tools, and automatic audit trail capabilities.

To meet these requirements, the Image Analysis System of the present invention is a general-purpose software product for 2D and 3D quantitative medical image analysis uniquely designed for drug and clinical trials. The application of this software product significantly reduces the time taken for lesion and tissue quantification compared to manual delineation. The reduction of time when using this system is described further in the following papers which are incorporated herein by reference:

[1] V. Chalana, L. Ng, L. Rystrom, J. Gee, and D. Haynor, "Validation of Brain Segmentation and Tissue Classification Algorithms for T1-weighted MR images," presented at Proceedings of SPIE Medical Imaging Conference, 2001.

[2] S. D. Pathak, V. Chalana, D. R. Haynor, and Y. Kim, "Edge-guided boundary delineation in prostate ultrasound images," IEEE Transactions on Medical Imaging, vol. 19, pp. 1211–1219, 2000.

[3] B. T. Wyman, L. Ng, B.-F. Sparks, and V. Chalana, "Novel convergence criteria for robust multi-modality image registration," proceedings of the ISMRM tenth scientific meeting, Honolulu Hi., 2002.

Medical images are also increasingly being used to extract quantitative endpoints, such as the size of a tumor, in clinical trials of drugs and devices. High resolution, three-dimensional computed tomography (CT) or magnetic resonance (MR) images provide unique views of anatomy and pathology permitting quantitative measurements that are not otherwise possible. Moreover, the quantitative nature and the relatively low variability in computing these end-points makes the use of images very attractive in clinical trials. Reducing the variability of an end-point reduces the sample size required resulting in significantly cheaper and faster randomized clinical trials.

The current practice in making measurements from medical images is by manual delineation. Manual delineation especially on 3D image series is painstakingly slow and expensive. Moreover, such manual delineation suffers from lack of consistency and reproducibility. Therefore, there is a need for automatic and semi-automatic 2D and 3D image segmentation tools. In addition, there is a need to extract shape and intensity features corresponding to the segmented regions.

For example, in pharmaceutical clinical trials involving images, a subject is typically scanned at different time points resulting in longitudinal image data sets. The ability to consistently interpret across the set of the scans is one of the most important requirements in clinical trials. Changes in patient positioning and alternative image acquisition setup may result in different image orientations compared to the baseline scan. Three-dimensional image registration simplifies the interpretation and correlation of findings between such studies.

Most imaging clinical trials collect large amounts of image data and other patient data from case report forms (CRFs). While there are electronic systems available for management of CRFs, the management of the large amounts of image data is not addressed in a robust and efficient manner. Moreover, recent regulations (21 CFR Part 11) from the Food and Drug Administration (FDA) require maintaining audit trails and electronic signatures for digital data management. Manually managing this data can be tedious. Moreover, the Food and Drug Administration (FDA) closely regulates the drug discovery and development process. Thus, any medical imaging analysis used to support a new drug application must be rigorously validated. This validation process can be simplified by the present invention.

Another important regulatory aspect of conducting a clinical trial with imaging involves ensuring the integrity of the electronic data. Document 21 CFR Part 11 and an FDA guidance document "Guidance for Industry—Computerized Systems Used in Clinical Trials" detail the regulations regarding the use of electronic records and signatures. Audit trails are a required component for conformance to these regulations An audit trail is a secure, computer generated, time-stamped electronic record that allows reconstruction of the course of events relating to the creation, modification, and deletion of an electronic record. While the images themselves must not be altered during the trial, the analysis of the images and, in particular, the generation of the segmentation overlays are considered electronic records which will be generated and modified by one or more users. Thus, an image processing system designed to support drug trials should automatically record the audit trail and ensure the security and integrity of both the data and the audit trail.

The present invention addresses the above needs and shortcomings of the prior art and comprises a computer workstation with an attendant software system for computer-assisted quantification of 2D and 3D medical images that significantly improves consistency of and reduces the time required for image quantification. The present system and method for mining quantitative information from medical images (here-in-after the "Image Analysis System") provides capabilities for registering and segmenting medical images in three-dimensions. With "Just-Enough-interaction" (i.e. semi-automatic), it assists the user in segmenting and contouring tissues such as gray matter, white matter, cerebral spinal fluid (CSF), tumor lesions, multiple sclerosis lesions, myocardium, and prostate.

System Architecture

As illustrated in FIG. 1, an Image Analysis System 100 of the present invention comprises an image system 105 that comprises a workstation 110, an image analysis module 120, which, in a preferred embodiment, is a software product comprised of a data registration module 125, a data segmentation module 130, and a feature extraction or quantification module 135. Each module may include one or more instructions which cause the computing resources to perform one or more operations/routines in order to implement the particular function of the module. The image analysis modules may also be implemented as one or more hardware circuits or pieces of hardware, such as one or more ASICs or may be a combination of hardware and software combined to provide the image analysis functionality. The Image Analysis System 100 further comprises a database management system 165 with an advanced radiology workstation graphical user interface (GUI) 115 within the image system 105 and an audit trail module 136 as shown. The workstation 110 shown is a well known computing device and the invention is not limited to any particular computing device and may be implemented on any computing device, such as a mainframe computer, a personal computer. etc. The workstation shown includes the well known computing resource (which are not shown in FIG. 1) such as one or more processors, memory, one or more persistent storage devices, a display device and one or more peripherals, such as a keyboard, a mouse, etc.

An overview of the system is as follows. A user accesses workstation 110 via GUI 115 to access image data 140 via a communications network 155, such as a WAN, LAN or INTERNET, or global network from a data base server 165 via a secure link 160 which uses a well known communications protocol that will not be described herein. The database server 165 is populated with images and relevant data from administrator 175 via a secure communications link 170 which uses a well known communications protocol that will not be described herein. The system may also include an image source 156 connected to the communications network 155 which may be used to generate external image data. To perform image analysis, the user imports the image data 140 into the image system 105 where the image is analyzed via the image analysis module 120. When the image analysis has been completed, the processed images 145 (which may include one or more of segmented images, registered images and quantitative features) are exported from the Image System 105 via the secure link 160 through the communications network 155 to the database server 165. The information is stored and quantified in the database server 165 for efficient and fast retrieval for the generation of reports, data mining and/or data analysis, regulatory submission or exportation to a client server or workstation 180. As shown in FIG. 1, audit trail data may be also exported from the image system 105 via the link 160 and stored in the database server so that the audit trail data is easily accessible. Alternatively data may be transferred to the subsystems using a system other than the WAN/LAN/Internet such as disk or CD.

The user interface GUI 115 is responsible for displaying and manipulating the images based on the user's commands. The image analysis module 120, as previously stated, includes the image segmentation module 130, the image registration module 125, and the feature extraction module 135. Each of these modules may implement one or more methods/routines/methods to achieve the desired results of image segmentation, image registration and feature extraction, respectively. The user interface 115 invokes these functions when a user selects the functions and displays the results of these modules to the user. The user interface 115 also contains the instructions to retrieve the images from the database 165 and store both the image analysis and feature extraction results in the database 165.

A standard off-the-shelf database management system (DBMS) is used to store all the audit trail data, image data, segmented images, and the extracted features, such as volumes of structures, etc. A standard DBMS offers many built in advantages such as, backups, redundancy, security, multi-user support, and client-server accessibility. The Open database connectivity (ODBC) protocol is used to communicate between the GUI 115 and the database 165—thus, any database management system, such as SQL Server (Microsoft Corp.) or Oracle (Oracle Inc.), can be utilized by the present invention to store the data and the invention is not limited to any particular DBMS.

The Structured Query Language (SQL) is employed to store and retrieve data from the database, although any type of a structured query language could be utilized. The SQL queries form the core of the powerful reporting mechanism provided by this system. The results of an SQL query forms a report that the system 105 outputs in various forms. These reports can be displayed in a tabular form in the GUI 115, copied and pasted into other applications, saved as HTML files, PDF files, GIF, TIF, JPEG, etc., for web reporting, or exported into SAS transport files for transfer into statistical analysis packages such as S-PLUS (Insightful Corp.) or SAS (SAS Institute). Since all the DICOM header information and all the quantitative measurement information are stored in the database, the resulting reports can be very sophisticated. For example, a report can be generated showing all the subjects in the database where a tumor decreased in size over time by more than 50%.

Initially, the database is populated directly by DICOM files from DBMS 165. DICOM files imported into the GUI 115 are parsed and stored in the database. The database schema was designed based on the DICOM image information model, where each Patient contains one or more studies, each study contains one or more series, and each series contains one or more images. The database schema can be modified, as appreciated by persons of ordinary skill in the art, to facilitate a multitude of various image information models as needed. An audit trail recording significant database and GUI 115 events is automatically recorded by the GUI 115 and stored in the database 165.

The database structure used in the present invention accommodates a standard well known DICOM format. The DICOM format includes a header which contains information about the images, and the image data. The header may have a variety of information about the study such as patient name, imaging modality, and image characteristics such as the pixel size. Using the pixel size from the DICOM header, the system may determine the size of a tumor since the tumor has been segmented in the image, each pixel size of the image is known from the DICOM header and the number of pixels in the segmented image multiplied by the pixel size is equal to the size of the tumor. The Image Analysis System parses the DICOM header information and populates the corresponding fields in the database.

Graphical User Interface

The present invention comprises a flexible, radiology-oriented GUI 115. Many of the GUI 115 features are those seen in standard radiology workstations. For example, multiple images in a series can be displayed in a flexible layout with a user-configurable number of rows and columns. The users can rapidly navigate the series of images using a Cine-mode navigation tool or a single-step navigation tool. In addition, the system reconstructs the image series data into a 3D volume. This reconstructed volume can be displayed in a multi-planar rendering (MPR) view where sagittal, axial, and coronal views of the same region are viewed together.

System Requirements

Most commercially available medical imaging workstations such as picture, archiving and communication systems (PACS) and 3D radiology systems were designed for the patient-care setting and emphasize visualization of the image data sets 140.

A feature common to both systems is the ability to support the transfer and reading of images stored in the DICOM (Digital Image Communications in Medicine) format. Also, both systems require the ability to review the images by domain experts with varying degrees of computer expertise—thus, an easy to use radiology oriented graphical user interface (GUI) is important. In addition, the ability to visualize the data in both 2D and 3D modes can assist in the proper interpretation of the images. Also, both systems require some form of a database management system in order to handle large quantities of data.

In addition to requiring the features found in patient-care oriented systems, medical Image Analysis Systems designed for clinical trials have several additional requirements. For example, in drug trials, there is a greater need to quantify results from the images resulting in additional requirements for these image analysis workstations. Before a pathological or a normal structure can be quantified, it must be segmented from the image. Thus, a variety of 2D and 3D image segmentation methods are needed in such a system. The appropriate choice of segmentation tool depends largely on the imaging modality and the features to be extracted. Once segmented, an array of calculations can be performed on the segmented regions to extract information such as volume, surface area, mean pixel intensity etc. Since clinical trials require statistical information across the studies, the ability to consistently and accurately quantify, correlate, and report this information is more important than in the patient-care environment where the analysis is often limited to determining the existence and location of a lesion(s).

Imaging during clinical trials has additional emphasis on examination of longitudinal data (which is data from different time intervals and structures are compared over a time interval). Often it is the differences in features, such as tumor volume, between time intervals that are most important. Thus, the software must provide for tracking and registration of longitudinal data. In addition, there must be the ability to quantify differences between data sets. This ability to track differences between data sets has direct application to the patient care setting in the area of treatment planning or disease monitoring, where multiple studies acquired at different time points are used.

Another difference between the analyses of data in a drug trial setting versus the patient-care setting is the need to analyze trends across patient groups. In the patient-care setting, each patient is studied independently from any other patient's findings. In the drug trial setting, the data must be grouped across subjects. The ability to store quantified results in a database and to perform cross-subject queries and create quantitative reports is essential for analysis of the study results.

An additional aspect in the present Image Analysis System 100 is the ability to find the appropriate balance between the amount of user interaction and full automation. While full automation is desirable, there are several reasons why it may not be practically applied for a drug trial. First, it is essential to have an expert in the analysis loop because a trained clinician can integrate a variety of information into the analysis that is not typically available to image processing methods. For example, the physician may have knowledge of the patient's history or the typical progression of the disease that can assist in the final analysis. Second, the validation of a fully automatic system is far more difficult than one which has oversight by a domain expert. Finally, fully automatic image processing methods are not perfect and can sometimes fail. Experts can often identify these failures and can easily correct the errant results. On the other extreme, completely manual methods are often subjective and result in poor intra-user and inter-user consistency. In addition manual methods are generally slow and tedious.

The approach taken with segmentation tools is to adopt the philosophy of using "just-enough interaction". Thus the tools permit semi-automation of the segmentation tasks, which improves the consistency, reduces the time to completion, and yet permit the expert to adjust the results as necessary.

Figure 2:
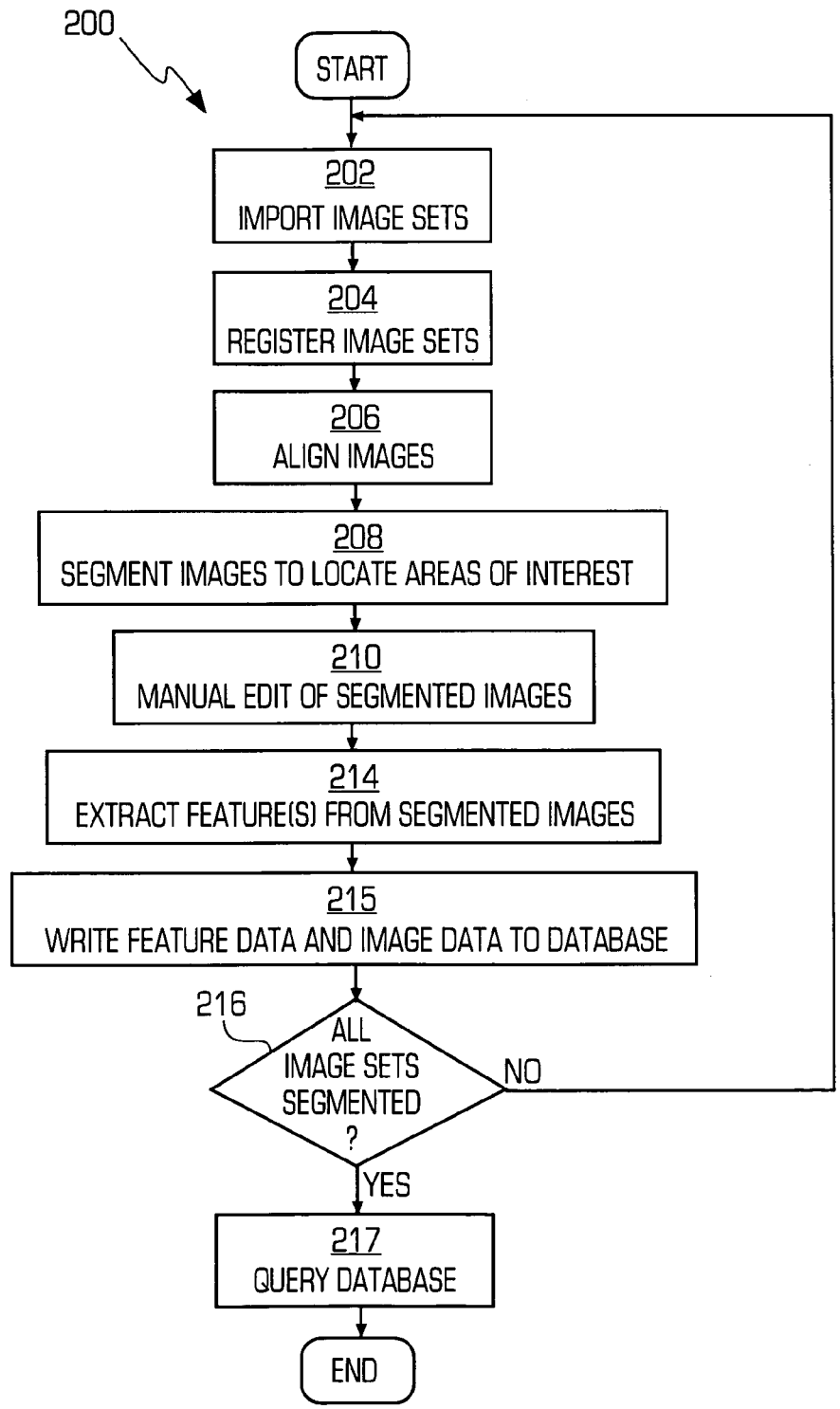
FIG. 2 is a flowchart illustrating a drug study process wherein the imaging system is being used.

An example of the Image Analysis System 100 in operation with respect to a multiple-sclerosis (MS) drug development study will be briefly described to illustrate the steps of the study and where the Image Analysis System is used within the process. FIG. 2 is a flowchart of a study process 200 and the example will be described using that flowchart. A pharmaceutical company with an MS drug typically recruits hundreds of patients with MS in Phase 3 of a clinical trial. In a randomized way, about half the patients are given the drug and other half are given a placebo. These patients undergo an MRI scan every three months while they are on treatment. Multiple MR image sequences with different MR acquisition parameters are acquired during each visit. The first goal of the data analysis is to measure the total MS lesion volume from the image sequences for each patient at each time point that they are scanned. The second goal of data analysis is to mine all the MS volume information to determine whether the MS drug is effective.

The Image Analysis System 100 of the present invention can be used for both the above data analysis tasks. The following steps are involved in the MS lesion volume computation task:

(i) For one time point, all the image sequences are opened and imported via the system software product of the Image Analysis System (step 202);

(ii) Image registration is applied to align the different sequences to one another (step 204);

(iii) The image sequences are also aligned to the baseline scan (step 206);

(iv) The multi-channel tissue classification/segmentation method is applied to find all the MS lesions in the entire image sequence (step 208);

(v) While looking at the image sequences from the current time point and the baseline, the automatically segmented and identified lesions may be manually edited by an expert to correct any errors (step 210);

(vi) If the segmentation is complete, the volume and other features for the edited lesions are computed using the feature extraction method (step 214); and (vii) The edited lesions and the quantitative information about them are saved into the database (step 215).

(viii) This process is repeated (segmentation) for other image data sets (Step 216) and then the database can be queried (step 217) to locate the studies that have a particular set of characteristics.

Image Registration

When imaging is used during the drug discovery or development process, the images are almost always acquired at different time points and are often acquired using more than one imaging modality. The image registration method 125 has three primary uses. First, registration can be used to align images acquired using different imaging modalities. Each modality may give different information regarding anatomy, pathology or function. Aligning this information assists the user in visualizing and interpreting the results. Without registration it is often difficult to spatially correlate findings from one image set to another image set acquired with different spatial orientations. The second use of registration serves as a preliminary step to multi-channel tissue segmentation. Even image series acquired during a single MRI exam can be mis-registered and small movements by the subject can result in the degradation of multi-channel tissue segmentation and failure to detect small structures. The third use of registration is for aligning images acquired at different time points. Aligning the images permits easier visualization and correlation of the changes. In addition, any overlays or segmentations generated for the image stack can be transformed during the registration process permitting quantification of the differences. Without registration, the user would be responsible for visually determining the spatial concordance of the segmentations.

Image Segmentation

In the present invention, any number of commercially available image segmentation methods can be incorporated into and work with the Image Analysis System. Following the concept of "just-enough-interaction", these methods combine the superior ability of a trained user to recognize structures of interest with the superior ability of computers to precisely and rapidly delineate these structures. Manual editing tools are available for editing the results of the segmentation method, should the expert user deem them necessary.

The segmentation methods implemented in the present system, and described in the following subsections are: seeded region growing, live-wire delineation, multi-channel segmentation, shape based interpolation, snakes, snakes used in conjunction with other tools and manual segmentation tools.

From the segmented results, the Image Analysis System is capable of extracting pertinent quantitative information, such as tissue volume, area, lesion diameter, and average pixel intensity. Using the registration tools comprising an integral part of the system, these quantitative measurements can be tracked in serial data. The Image Analysis System further comprises a registration method capable of significantly faster registration of 3D image data. The registration method is described more fully in U.S. patent application Ser. No. 10/063,834, filed on May 16, 2002 and entitled "SYSTEM AND METHOD FOR DETERMINING CONVERGENCE OF IMAGE SET REGISTRATION" which is owned by the same assignee as the present invention and is incorporated herein by reference.

The present invention further integrates the database management system 165 (DBMS), as shown in FIG. 1, that stores both the image data and the quantitative information extracted from the image data. The database management system 165 not only enables persistent storage of image and other patient data, but also lets the system be used as an advanced medical imaging mining platform.

The system also provides manual painting tools to initialize the segmentation methods or to correct the automatic or semi-automatic segmentation results. The user can paint regions in any of the 2D or 3D views. Various line and polygon drawing tools are also provided for manual annotations. An additional aspect of the present system is that the painting can be done in 2D and in 3D and both views are always synchronized. Two-dimensional overlays are interpolated to create three-dimensional overlays and three-dimensional overlays are sampled to create two-dimensional overlays.

Figure 3:
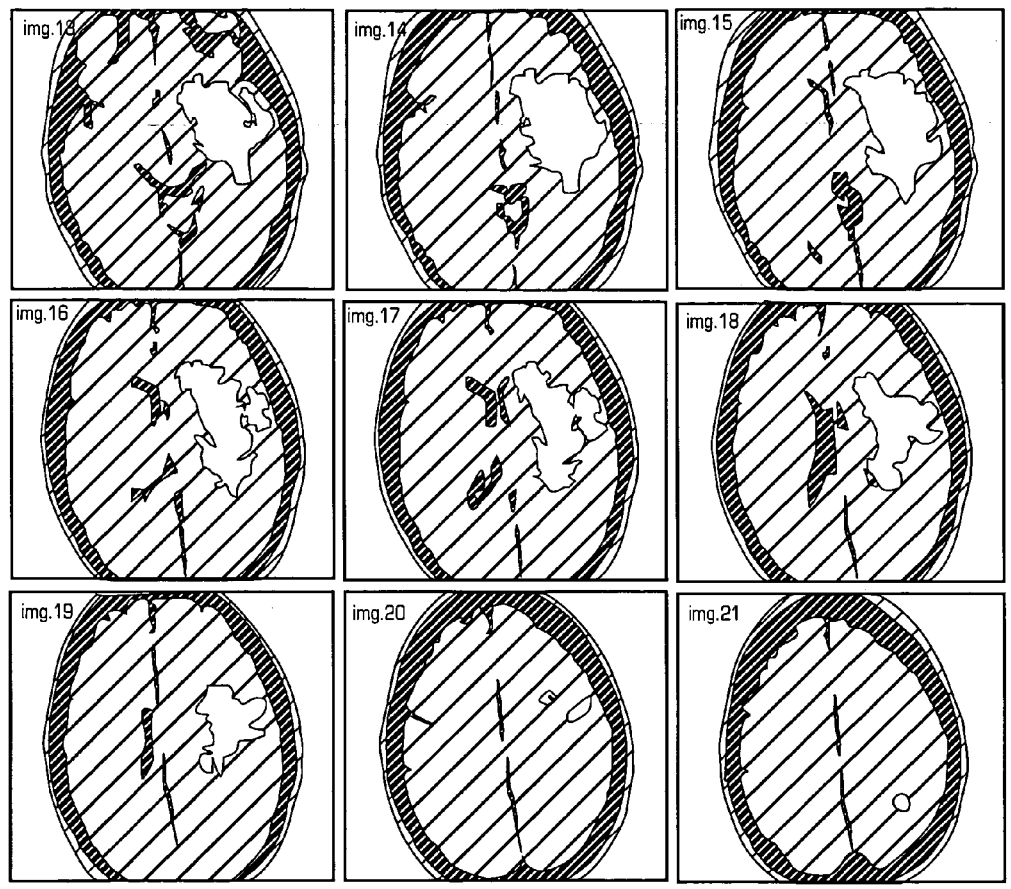
FIG. 3 depicts two dimensional overlays in a series of images representing a tumor.
Figure 4:
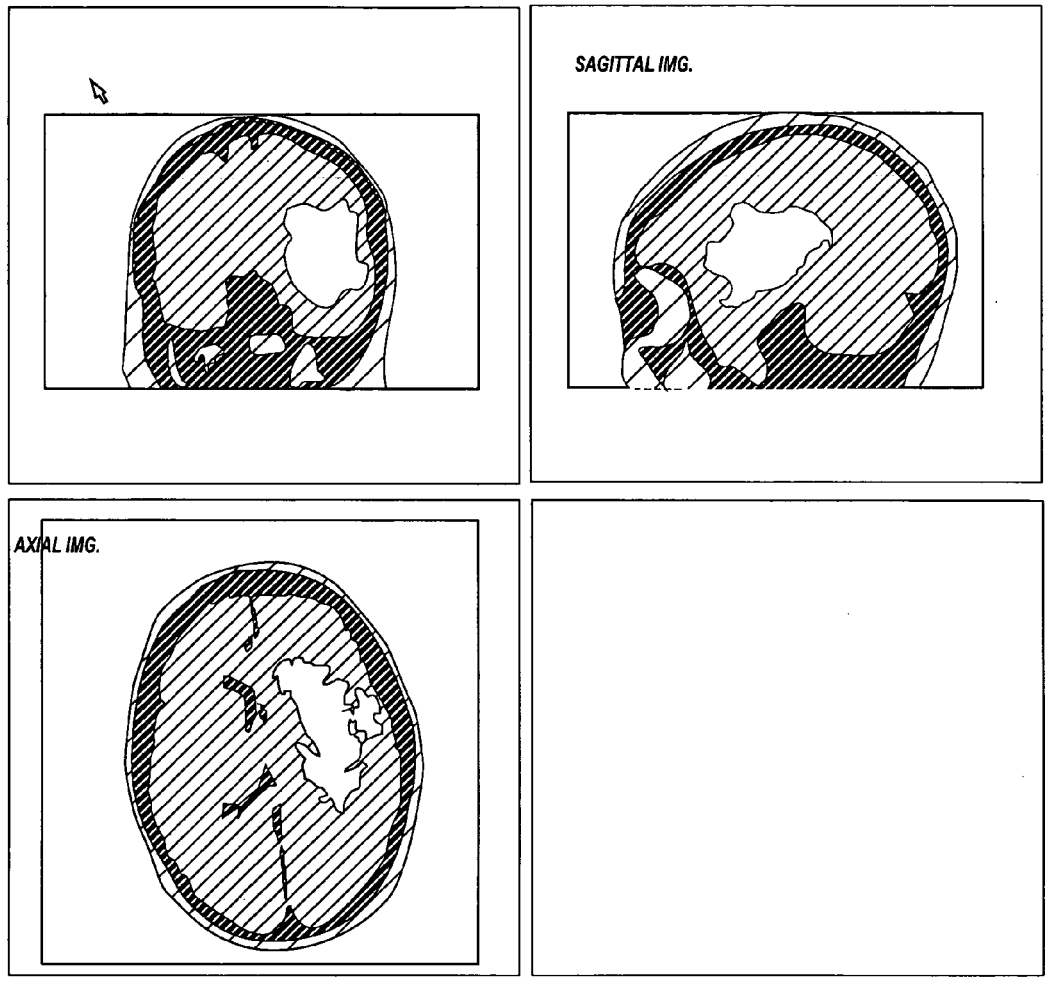
FIG. 4 depicts corresponding three dimensional overlays shown in a Multi-planar reformatted image set of the two-dimensional overlays of FIG. 3.

The image segmentations are displayed as color overlays on the original images. These overlays can be displayed in a region mode or in an edge mode. In the region-mode the entire overlay region is showed filled with a selected color as shown in FIG. 3. In the edge-mode, only the boundaries of the region are displayed as overlaid on the original image as shown in FIG. 4. Both display modes are useful in different scenarios and the present system allows the user to rapidly switch between the two modes. The user can vary the degree of translucency of the regions as well as the borders from opaque to transparent.

Figure 5:
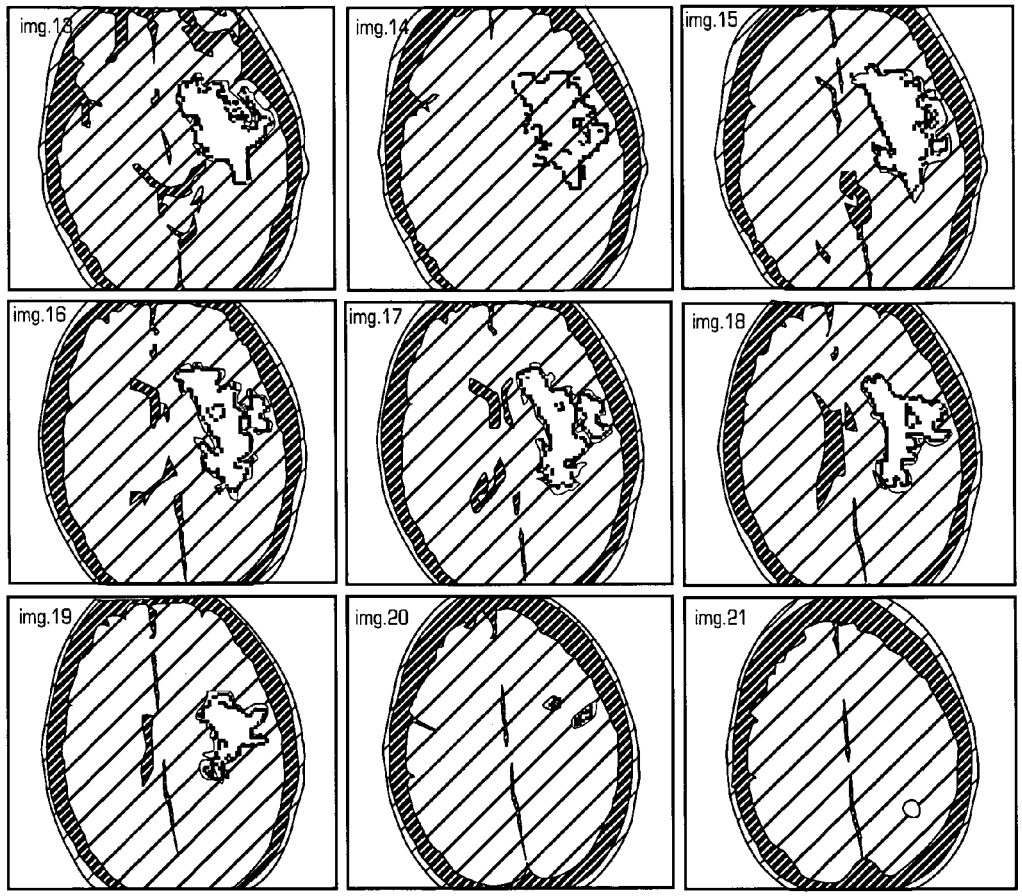
FIG. 5 depicts an edge mode representation of the tumor as shown in FIG. 3.
Figure 6:
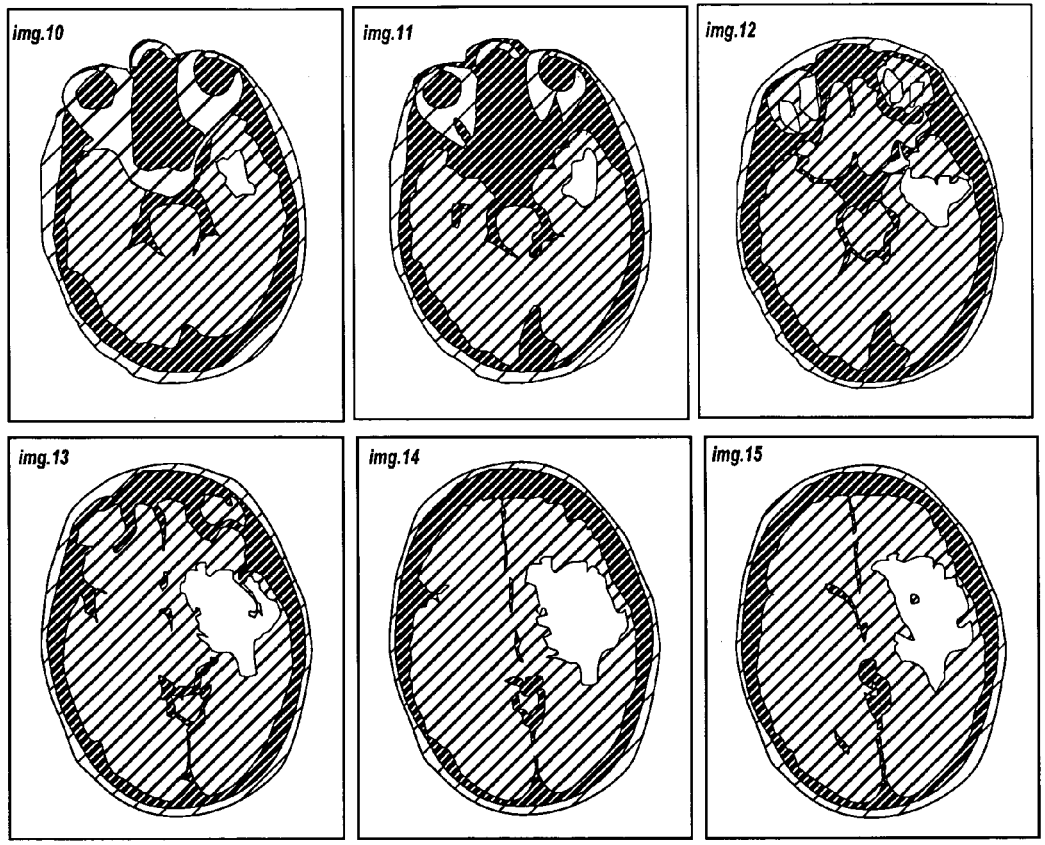
FIG. 6 depicts a 2×3 layout of an image series, of the present invention.

The aspects of the Image Analysis System 100 such as 3D and 2D painting, and region and edge-mode display, are accomplished through the use of a data structure and associated methods to represent the overlays. The following are aspects of the data structure:

1) the overlays are represented as 8-bit images (as opposed to representing them as polygons which is common). Therefore, an overlay can have up to 255 different colors (or unique regions);

2) an image can have many different overlay layers;

3) Every overlay layer is defined by two data structures—a two dimensional image stack (for display in stacked-mode) and a three-dimensional volume (for display in volume or MPR mode);

4) the two dimensional and the three dimensional representations of an overlay layer are always kept in synchronization through the use of interpolation and sub-sampling methods. An image interpolation method is used to create the 3D volume from the 2D stack of images—simply linear interpolation between corresponding image pixels is used in this method as is well known and the invention may be used with various other well known methods. A sub-sampling method is used to extract 2D image stacks from the 3D volume as is well known and the invention may use various well known methods to accomplish this result. Each 2D image in the image stack saves its location in the 3D volume and that location is used to extract a slice from the 3D volume; and 5) the edge mode display is accomplished through the use of well known edge extraction methods applied to the overlay image. An additional aspect of the graphical user interface 115 is the flexibility of the layout tool. FIGS. 3 and 5 are displayed in a 3×3 layout of the images in the series—3 rows and 3 columns. The Image Analysis System provides the user with the flexibility to change the layout to any desired layout—for example a 2×3 layout is shown in the FIG. 6 or a 2×2 layout shown in FIG. 4.

Figure 7:
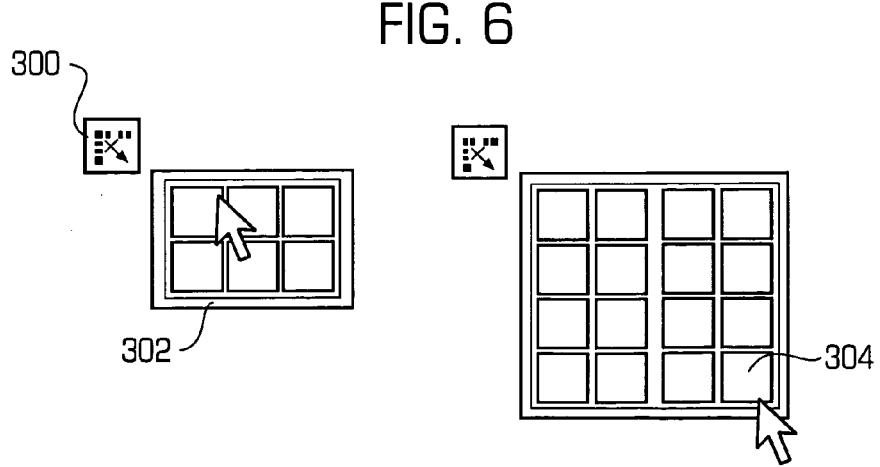
FIG. 7 illustrates a layout change process in accordance with the invention.

An aspect of this feature is the way in which the layout change is initiated from the GUI 115. In most existing systems, either the layout is fixed at 2×2, 3×3, etc. or the user is required to explicitly type in the number of rows and number of columns of images to display. In the present system this is accomplished by the user interface 115 as follows (and as shown in FIG. 7):

1) the user presses a layout change toolbar button 300 first;

2) after pressing that button, the user drags the mouse a small layout preview window appears next to the layout change toolbar button. This small layout preview window looks like a preview window 302 shown in FIG. 7;

3) as the users drag the mouse to the bottom of the screen new rows are added and they drag it to the right of the screen new columns are added in the preview window. Dragging the mouse to the left or to the top of the screen removes columns or rows respectively (See preview window 302 which is a 3×2 display and preview window 304 which is a 4×4 display);

4) once the user has the desired layout displayed in the small preview window, they release the mouse button and the image layout on the screen updates to same layout as in the preview window.

Yet another aspect of the graphical user interface 115 is a flexible splitter between the various image panes. In most existing systems, the size of the different panes within a multi-image window are fixed and the user does not have the flexibility of changing the sizes of the panes. It is sometimes very useful to have different panes of different sizes within a display window.

Figure 8:
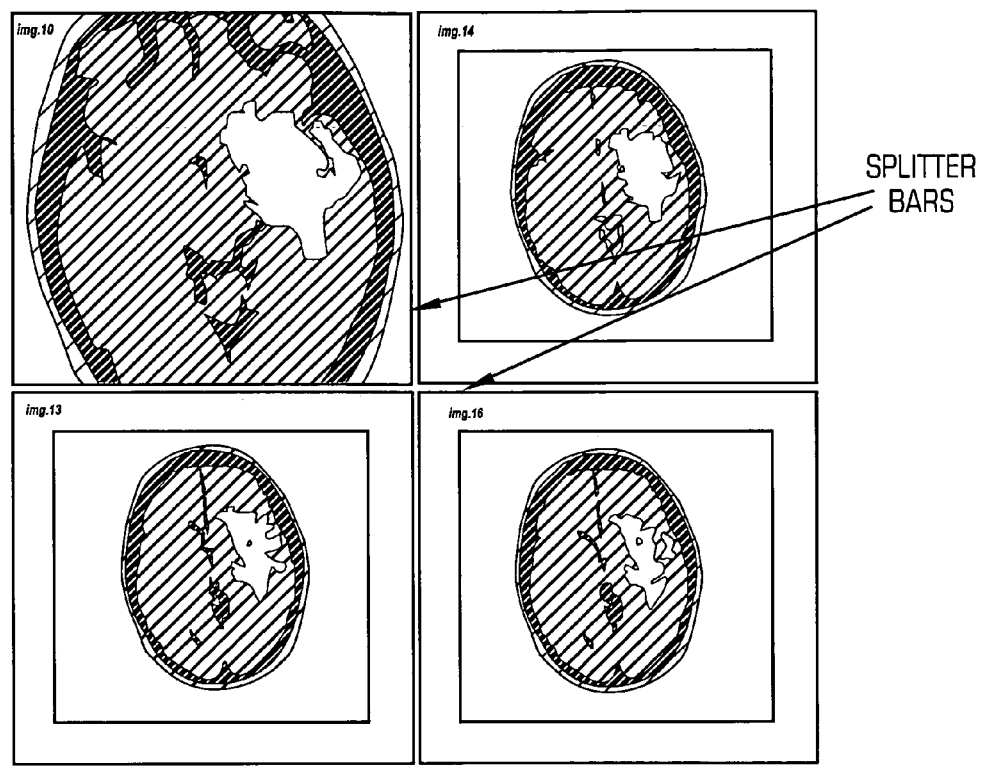
FIG. 8 depicts a 2×2 image layout displaying a truncated larger image.
Figure 9:
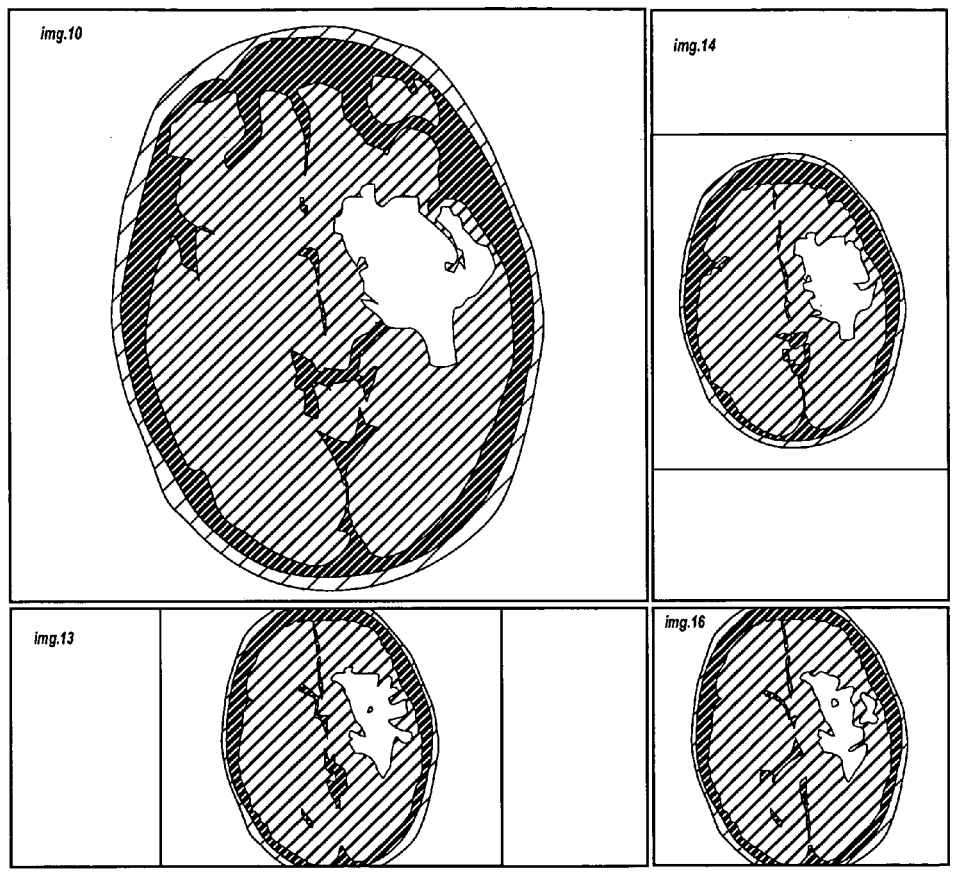
FIG. 9 depicts the 2×2 image layout of FIG. 9, wherein the window has been expanded to show the entire enlarged image without truncation
Figure 10:
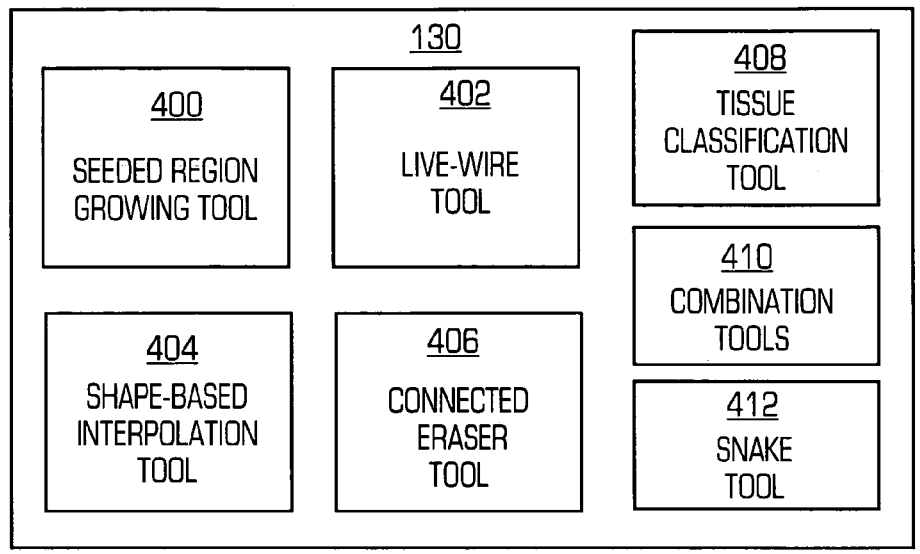
FIG. 10 is a diagram illustrating the segmentation module tools in accordance with the invention.

In a series of images being displayed in a 2×2 layout for instance, if the user wishes to display the first image in a larger size than the other images. If the panes are always the same size and cannot be modified then the result is as shown in FIG. 8, where the entire top-left image cannot be displayed without enlarging the entire window which is undesirable. A flexible splitter 610 between the panes allows the user to display the different panes in different sizes as shown in FIG. 9. In FIG. 9 the flexible splitter allows the user to display the entire top-left image and still view the other three images without changing the total window size.

Segmentation Module

Figure 11:
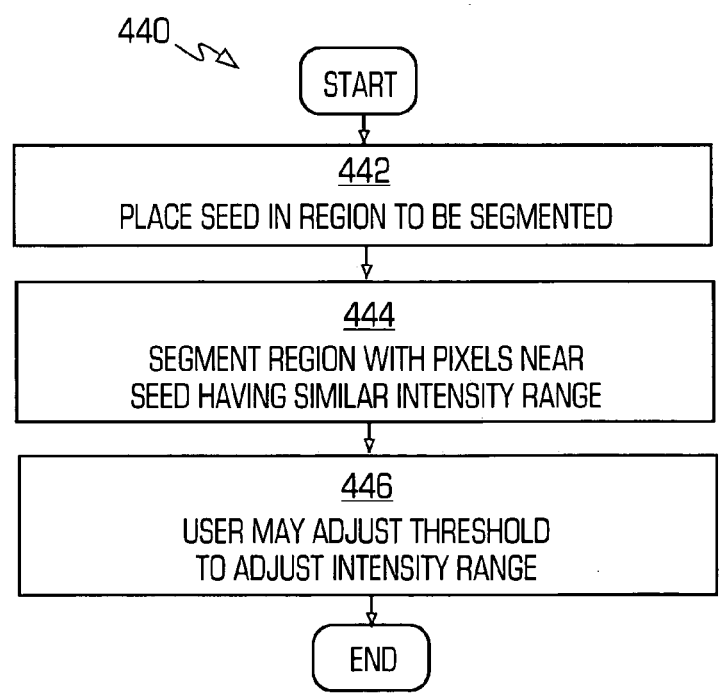
FIG. 11 is a flowchart illustrating a seeded region growing method in accordance with the invention.

The segmentation module in the present system provides an array of tools capable of being used in combination for image segmentation. As shown in FIG. 11, the segmentation module 130 may include manual segmentation tools, a seeded region growing tool 400, a live-wire tool 402, a shape-based interpolation tool 404, a connected eraser tool 406, a multi and single tissue classification tool 408, combination tools 410 and a snakes tool 412. Each of these tools will be described below in more detail.

Manual Segmentation Tools

The system also provides manual painting tools to initialize the segmentation methods or to correct the automatic segmentation results. The user can paint regions in any of the 2D or 3D views using a paintbrush tool with a user-variable size. Or various regions can be delineated with manual polygon tool. Various line, point and polygon and ellipse drawing tools are also provided for manual annotations. These annotation tools automatically calculate the distances or areas of the objects.

Seeded Region Growing Method

Figure 17:
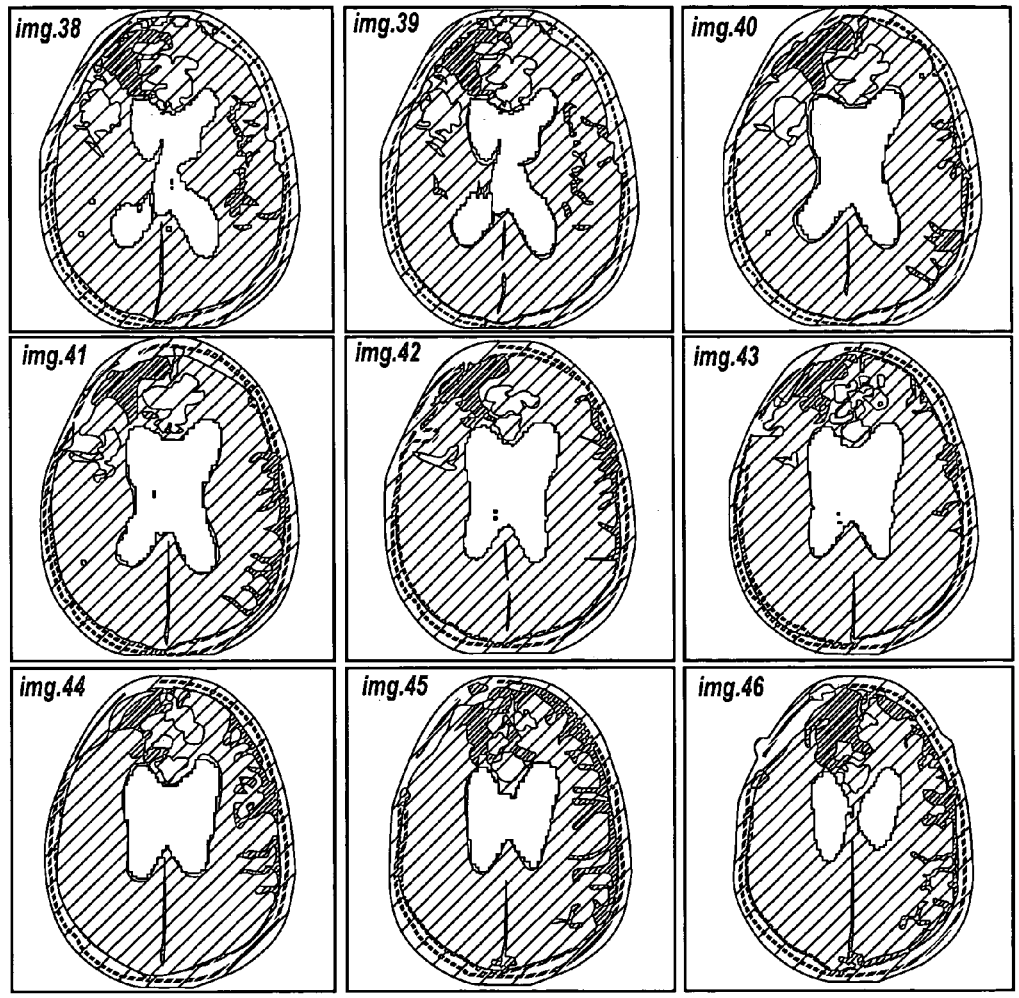
FIG. 17 illustrates the use of the shape-based interpolation to delineate the ventricles on all the 9 image slices.

Seeded region growing, also referred to as seed-fill, is shown in FIG. 11. While utilizing the seeded region growing tool, the user clicks somewhere on the object to be delineated as shown in FIG. 17 which describes a seeded region growing method 440. The method results in the delineation of the entire object, either in 2D or in 3D. The seeded region-growing method permits the user to place a seed point within regions to be segmented by clicking on the image as shown in step 442. The method then segments a connected region around the seed point in step 444 where all the pixels (x) in this region satisfy the following criterion of equation (2) as follows:

$$(m-r) \leq f(x) \leq (m+r) \qquad \text{EQ(2)}$$

wherein f(x) is the intensity value of pixel x, m is the mean intensity of the region computed from a small neighborhood around the seed point, and r is a user-adjustable range value. Thus, this method segments all the connected pixels within the range of values around the mean of the seed point. The present system provides both 2D and 3D versions of the method.

The user can then adjust the threshold of the seed fill to fine tune the end results in step 446. This adjustment essentially changes the limits (m−r) and (m+r) in EQ 2. Some options for threshold adjustment include changing r only, having separate upper and lower bounds, permitting the independent adjustment of both m and r.

Live-Wire Delineation

Figure 12:
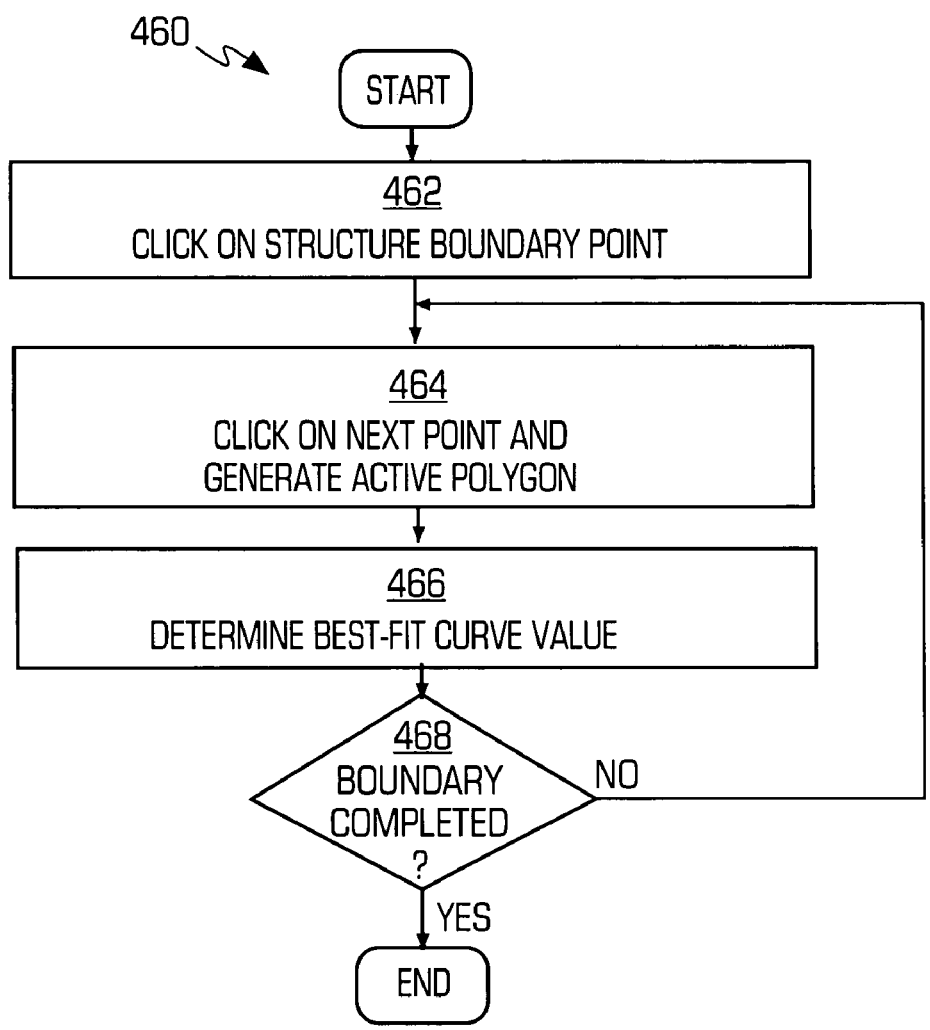
FIG. 12 is a flowchart illustrating a live-wire segmentation method in accordance with the invention.

Live-wire is an interactive tracing tool used for precise delineation of structure boundaries with minimal user effort. The live-wire tool (a live wire method 460 is described with respect to FIG. 12) allows the user to rapidly delineate an object of interest by clicking only on a few selected points on the boundary of the object. The user gets interactive feedback about the location of the boundary as they move the mouse. The user starts tracing with live-wire by clicking on any point on a structure boundary in step 462. As the mouse is moved around the image, an active polygon connects the current cursor location with the last-clicked mouse point along the strong gradient edges in the image in step 464. As the user moves the mouse near the boundary of the structure, the method traces the precise boundary of the structure.

The live-wire method is a graph-matching method that computes a best-fit (least cost) curve in step 466 between the most recent mouse position and last clicked vertex. The cost of the curve is defined by the proximity of the curve to the high gradient points on the image. The closer the curve is to strong edges in the image, the lower the cost of the curve.

Shape-Based Interpolation

A shape-based interpolation method is used to rapidly create 3D segmentation from a few 2D segmentations by interpolation. The user draws two-dimensional contours on selected image slices in a 3D sequence of images. The shape-based interpolation tool interpolates the contours between the slices on which the contours are drawn. Such a feature is useful in tasks such as vessel segmentation where the shape change between several image slices is gradual and can be well-approximated using shape-based interpolation.

The combination of the live-wire and shape-based interpolation tool provides a powerful three-dimensional segmentation method. The user can outline a structure using live-wire on two or more images in a series of images and can apply the shape-based interpolation tool to interpolate between the slices.

Figure 13:
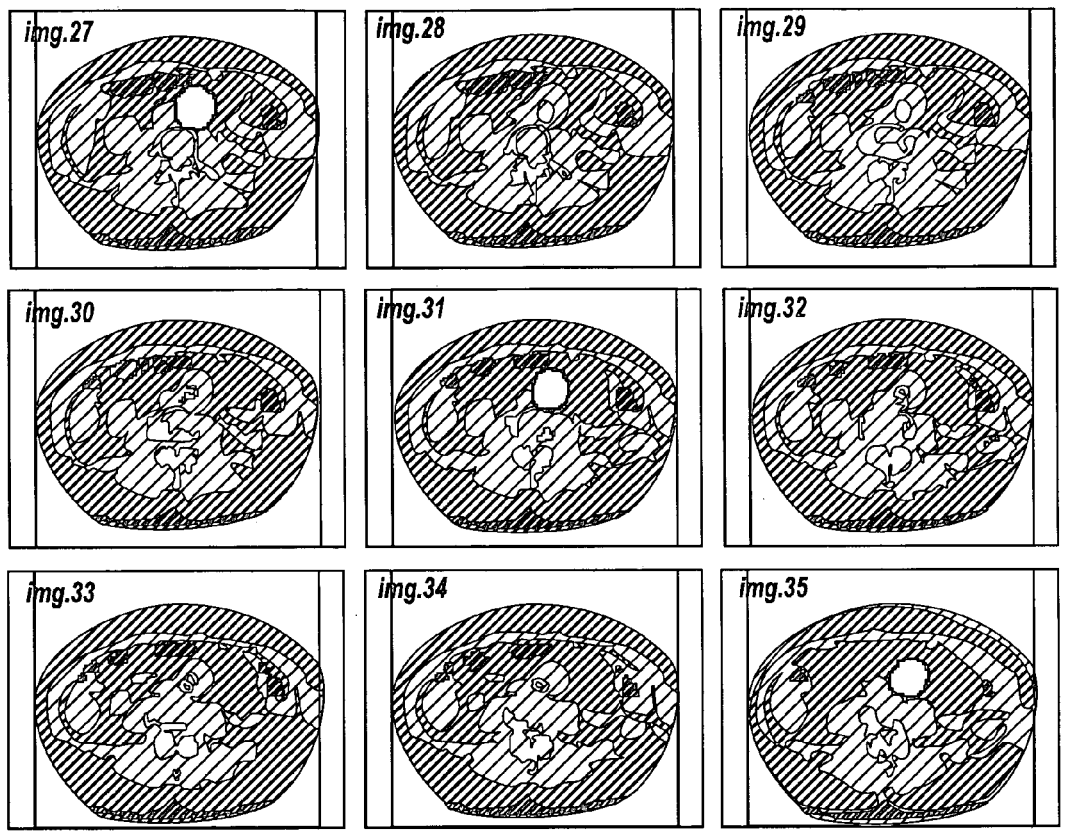
FIG. 13 depicts the application of the live-wire tool on image slices 83, 87 and 91 to delineate a structure (the abdominal aortic aneurysm), of the present invention.
Figure 14:
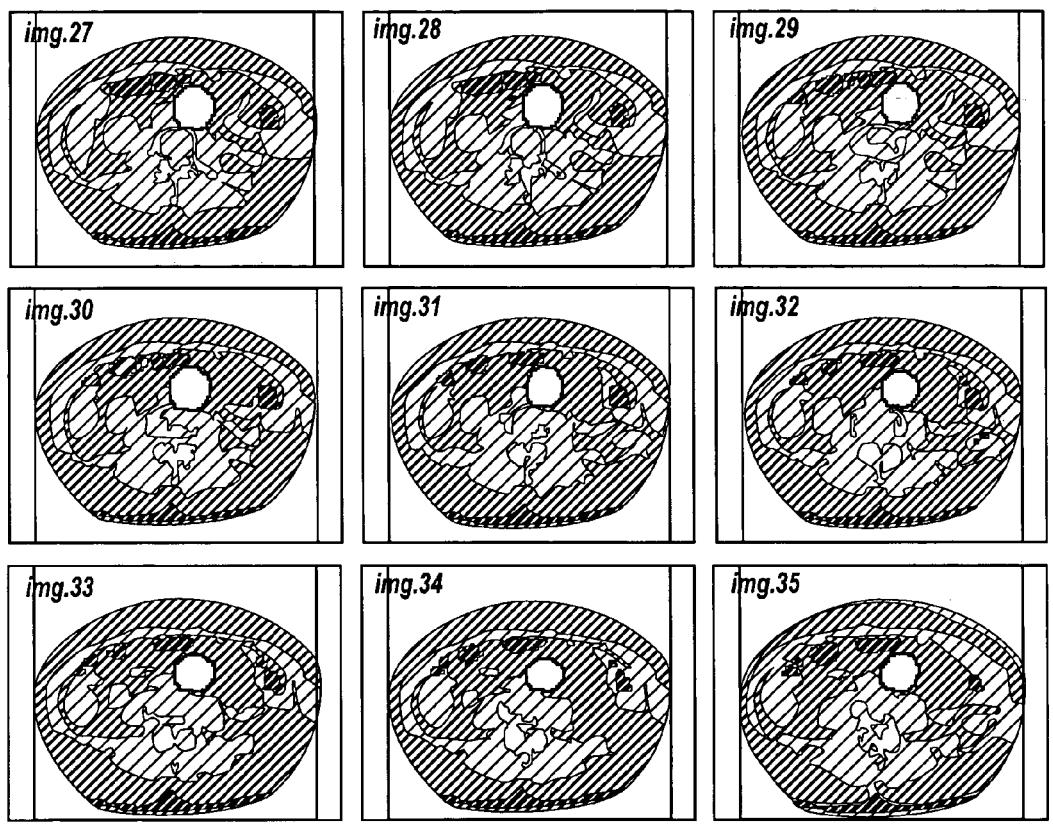
FIG. 14 depicts the application of the shape-based Interpolation tool on image slices, 83,87 and 91 to automatically delineate the structure of all the slices between slices 83, 87, and 91, of the present invention

FIG. 13 illustrates the use of the live-wire tool on the image slices 83, 87, and 91, to delineate a structure (the abdominal aortic aneurysm). FIG. 14 illustrates the use of the shape-based Interpolation tool used to automatically delineate the structure all the slices between slices 83, 87, and 91.

Figure 15:
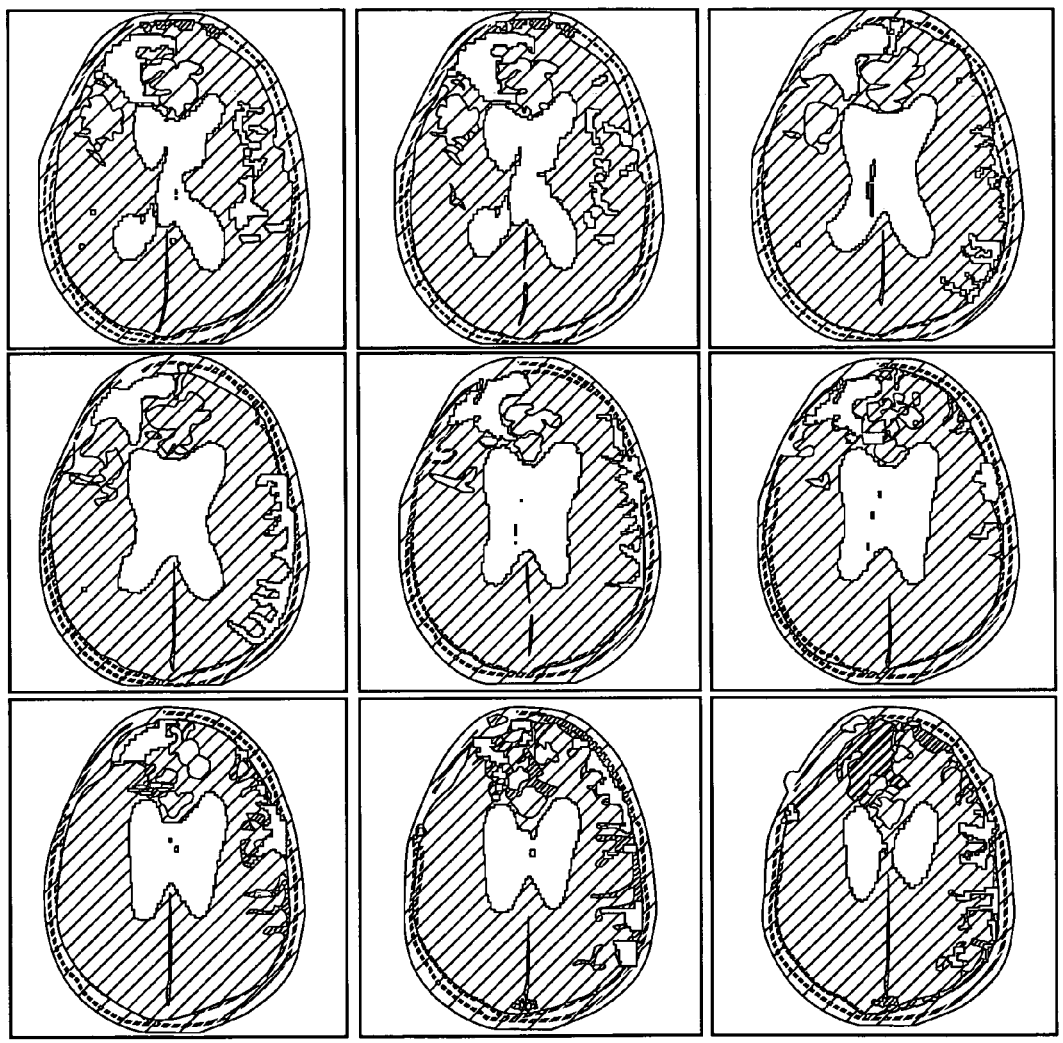
FIG. 15 depicts the use of the use of seeded region growing and the detection of regions outside the ventricle.

The combination of 2D seeded region growing and shape-based interpolation also provides powerful three-dimensional segmentation. In particular, the user can outline a structure using shape-based interpolation on two or more images in a series of images. Then they can apply the shape-based interpolation tool to interpolate between the slices. Sometimes, the use of this method is necessitated in cases where the 3D seeded region growing is not applicable. FIG. 15 depicts the result of 3D region growing and it results in the detection of the cerebro-spinal fluid outside the brain in addition to the ventricle, therefore, 3D region growing would not be the optimal tool for this particular problem.

Figure 16:
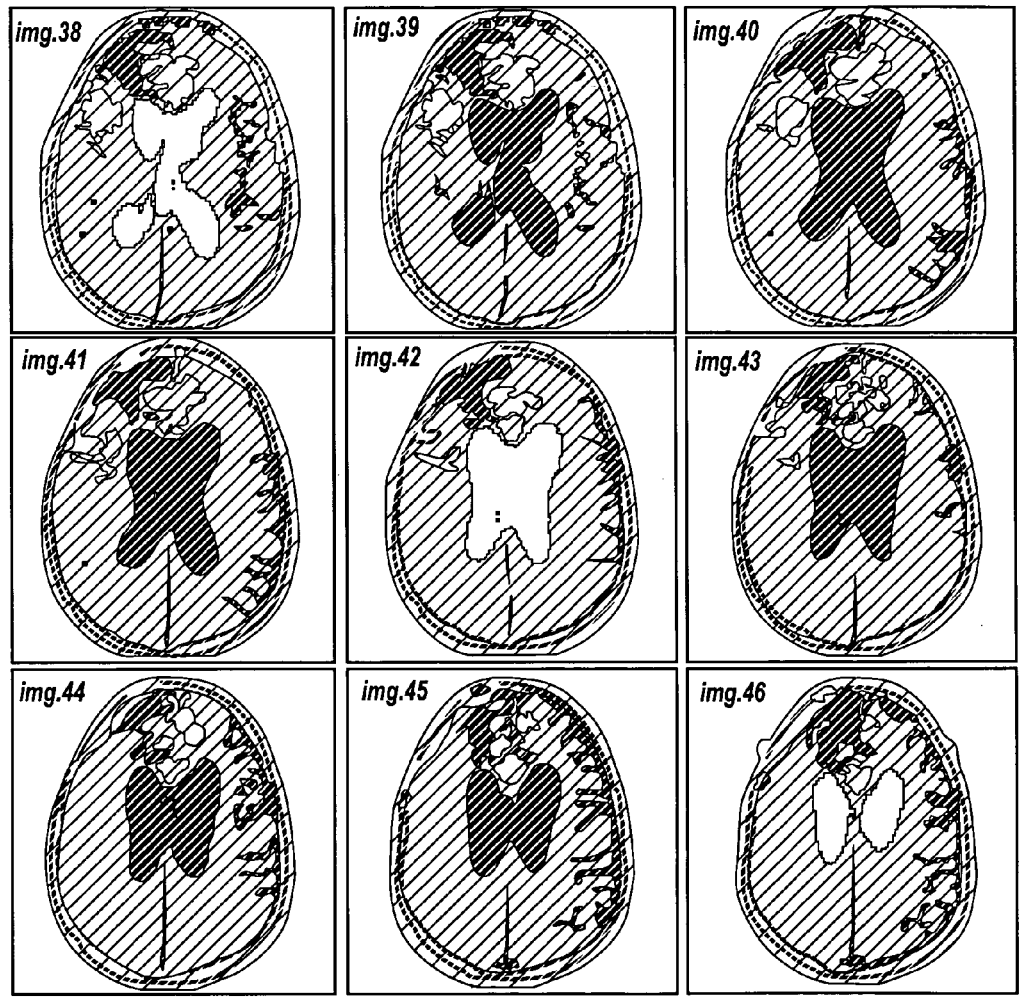
FIG. 16 illustrates the use of the 2D Seed Fill tool to delineate the ventricle in the brain in 3 of the 9 image slices.

FIG. 16 and FIG. 17 depict the approach of the present invention wherein a 2D region growing is used on 3 slices and the result is interpolated to the other slices in the image sequence. FIG. 16 illustrates the use of the 2D Seed Fill tool to delineate the ventricle in the brain in 3 of the 9 image slices and FIG. 17 illustrates the use of the shape-based interpolation to delineate the ventricles on all the 9 image slices.

Connected Eraser Tool

Figure 18A:
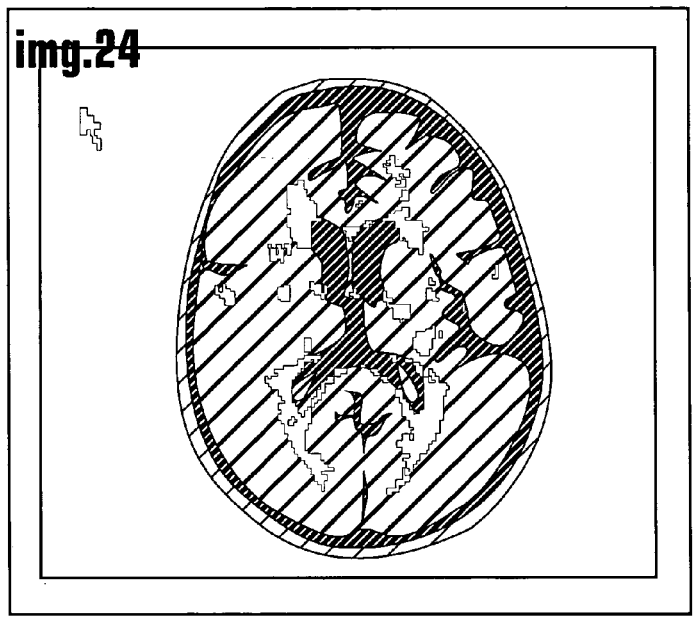
FIGS. 18(A) and 18(B) illustrates the use of the erase connected tool of the present invention.
Figure 18B:
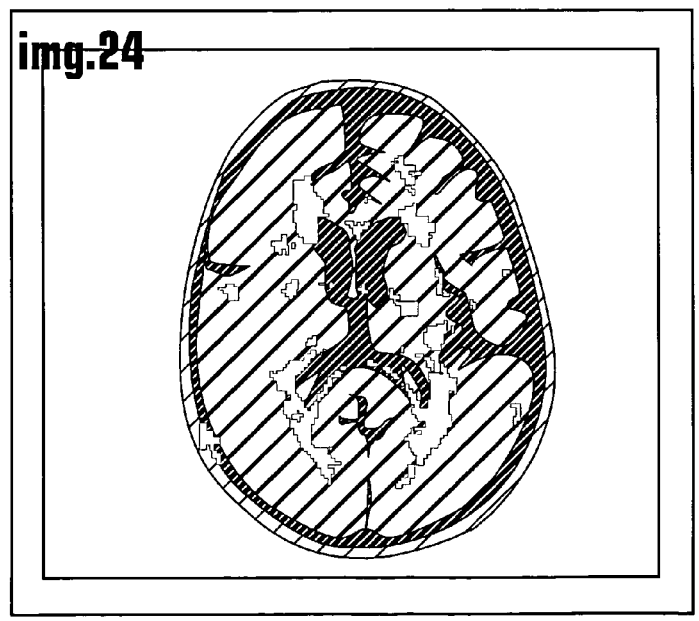

The connected eraser is similar to the region-growing tool, except it is used for erasing regions previously drawn. The user clicks somewhere on a previously painted region to be deleted and then the entire overlay connected to the clicked point is erased. An example of using the erase connected tool to correct the results of tissue classification or other segmentation methods is shown in FIGS. 18(A) and (B). FIG. 18(A) depicts the result of tissue classification on one of the images, wherein the scalp area is falsely labeled as a lesions also. By simply clicking on a region of the scalp using the erase connected tool, the entire scalp area is erased as shown in FIG. 18(B). Thus the connected erase tool allows the user to quickly edit the results of tissue classification.

Multi- and Single-Channel Tissue Segmentation

The tissue classification tool in the present system enables the identification of one or more tissue types in an entire image sequence. The user first identifies key tissue types as exemplars. The method uses these exemplars as training data and identifies the trained tissue types in the entire image sequence. This method works with single channel data and it also works with multi-channel data.

Since they use the same methods we will simply use the term multi-channel segmentation to generically refer to both methods. While the seeded region growing method finds regions that are spatially limited and connected to the seed point, the tissue segmentation method is useful for delineating tissues that are distributed throughout the image series. This tool uses multivariate statistics to combine multiple channels of information, such as T1 and T2-weighted MR series. Combining multiple channels of data can increase the discrimination between different tissue types, thus leading to improved segmentation. If multiple series are present for the same study and the series give complementary pieces of information, all of these series can and should be used for tissue classification to give more accurate results.

Figure 19:
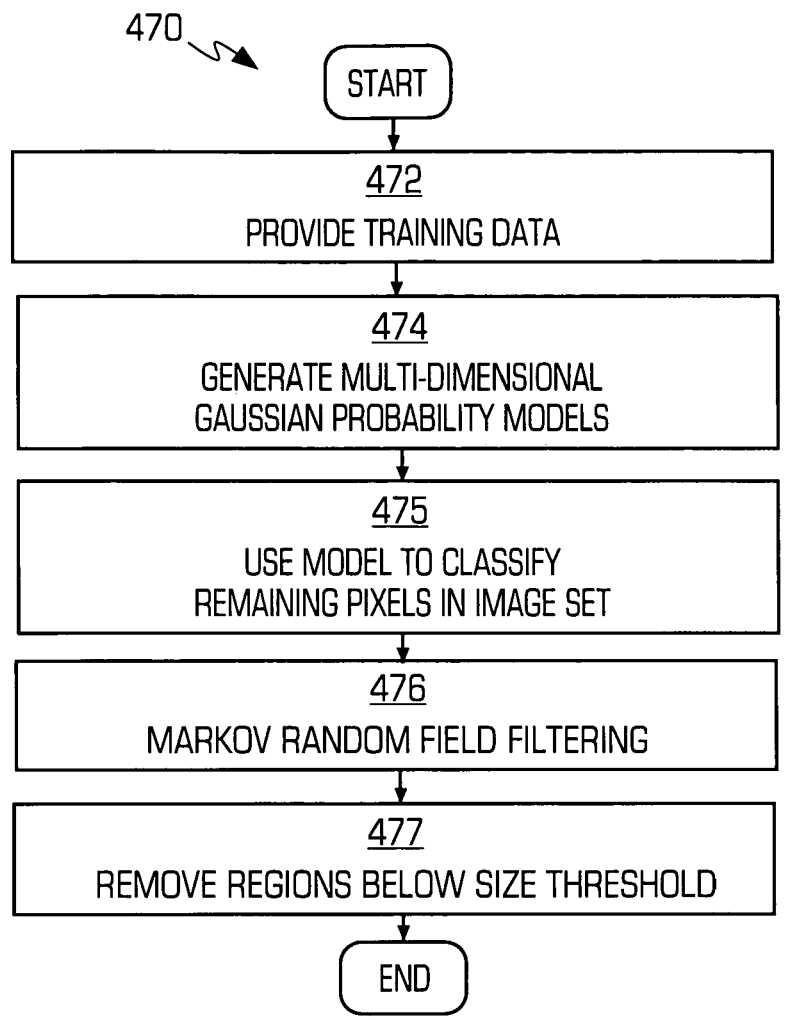
FIG. 19 is a flowchart illustrating a multi-channel tissue segmentation method in accordance with the invention.

A multi-channel tissue segmentation method 470 in accordance with the invention will be described with reference to FIG. 19. The first step in multi-channel tissue segmentation is to provide training data in step 472. This training data consists of annotations of exemplar regions for one or more tissue types present on the image. The user can use the manual painting tools and/or any of the computer-assisted segmentation tools to provide regions for training. Based on this training data, multi-dimensional Gaussian probability models are generated for each tissue types in the training data in step 474. The user can either specify a probability threshold value on a single Gaussian model or can apply a maximum likelihood (ML) classifier. In step 475, the model may be used to classify the remaining pixels in the image set. An optional Markov Random Field (MRF) filter can be used to further refine the ML results in step 476. Finally, a size filter is provided where all connected regions smaller than the user-specified size threshold are removed in step 477. This filter can be used to improve the results by eliminating small, segmented regions which may result from image noise.

Figure 20:
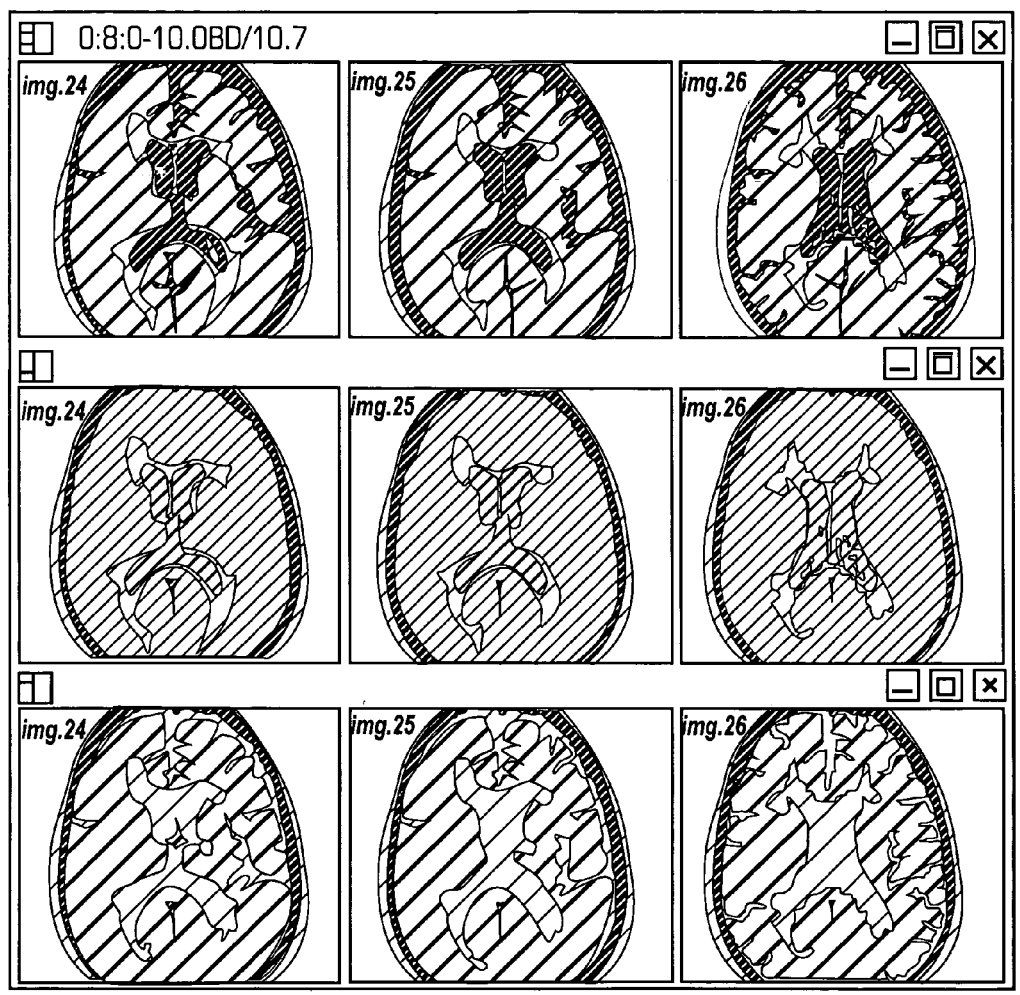
FIG. 20 illustrates a multi-channel series of images, wherein each row represents one channel of information while each column represents a unique slice position in 3D space of the present invention.

FIG. 20 illustrates a multi-channel series of images, wherein each row represents one channel of information while each column represents a unique slice position in 3D space. The top row is a FLAIR MR sequence, the middle row is the Proton Density (PD) sequence and the bottom row is the T2-weighted sequence.

Figure 21:
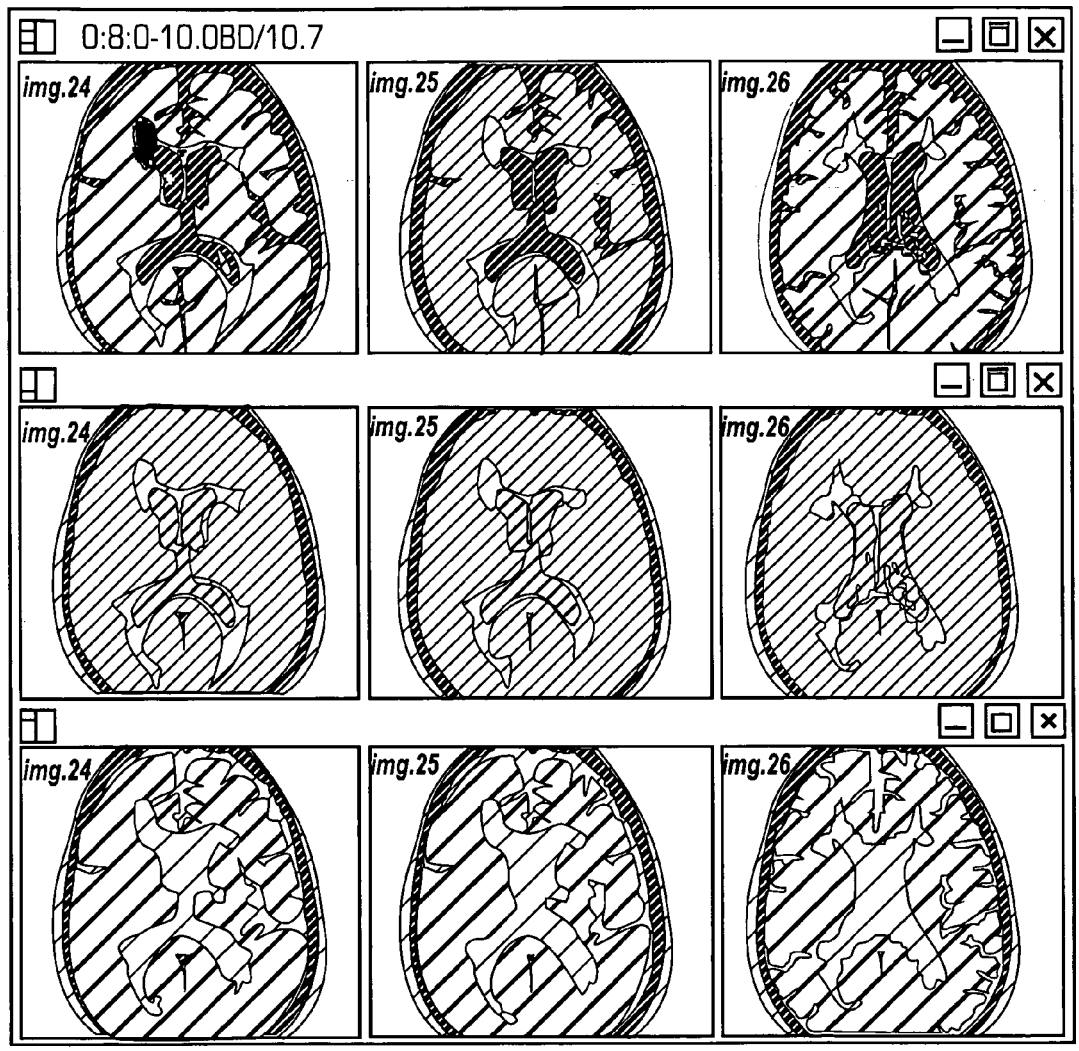
FIG. 21 illustrates the use of the seeded region growing method used to mark an example MS lesion on the FLAIR sequence.

FIG. 21 illustrates the use of the seeded region growing method used to mark an example MS lesion on the FLAIR sequence. This region is used to train the multi-channel segmentation method.

Figure 22:
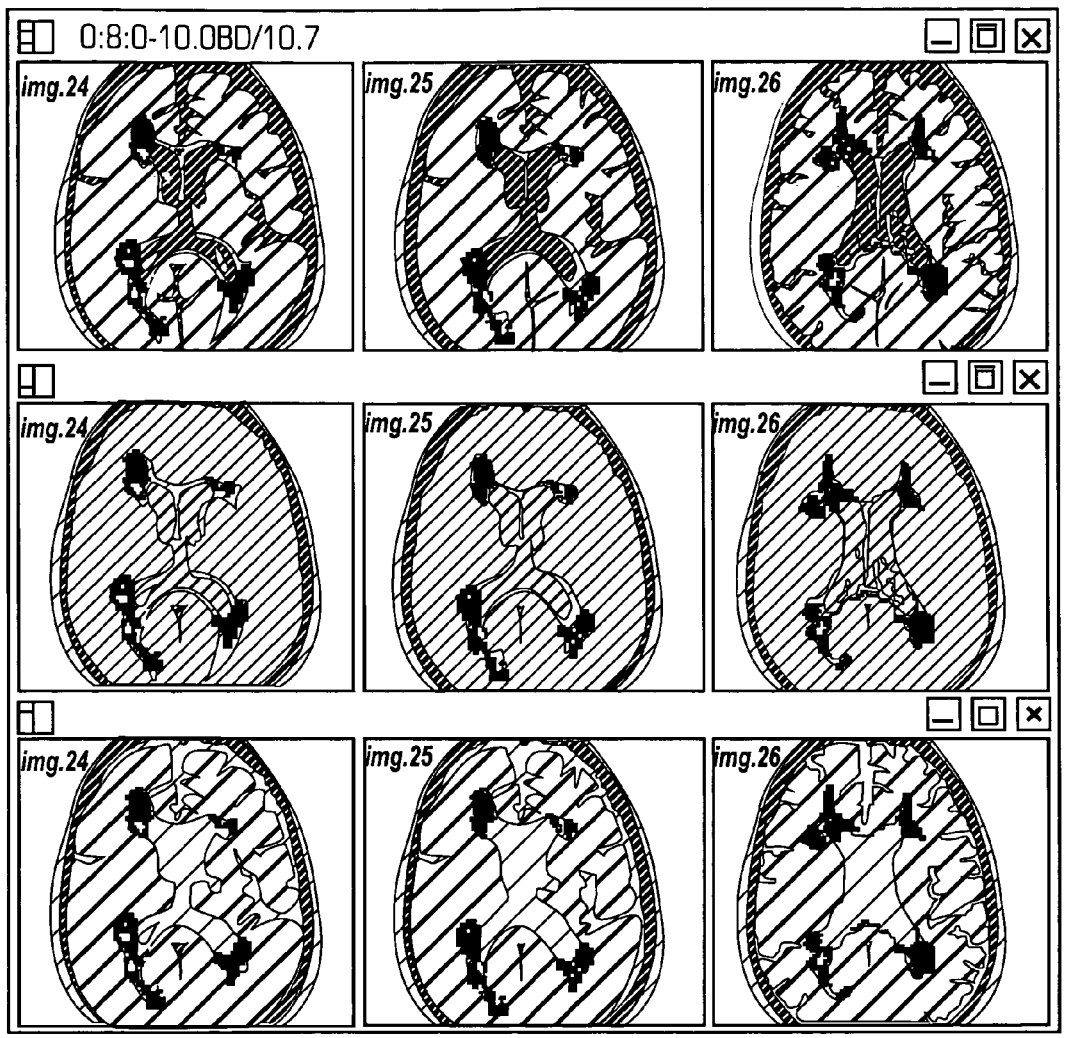
FIG. 22 illustrates that by using the previously marked region, of FIG. 26, as training, the multi-channel tissue segmentation method locates all MS lesions in the entire image sequence.

FIG. 22 illustrates that by using the previously marked region, of FIG. 21, as training, the multi-channel tissue segmentation method locates all MS lesions in the entire image sequence. These lesions are labeled on all the channels that were used in the method.

Snakes

Figure 23:
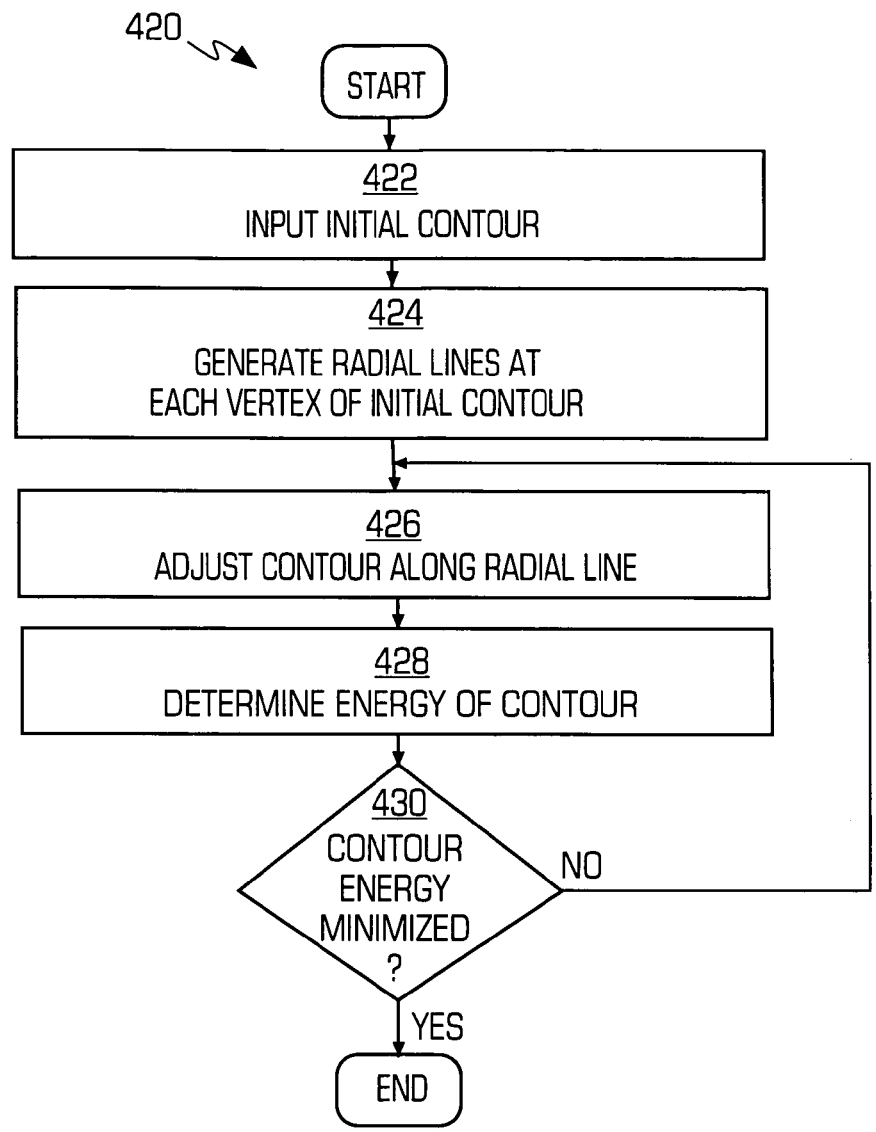
FIG. 23 is a flowchart of a snakes segmentation method in accordance with the invention.

In a further aspect of the segmentation module of the present invention, a segmentation method called "snakes" is also incorporated into the present invention. The snakes method will be described with reference to FIG. 23. The snakes method functionally performs the following steps in its segmentation method. The user specifies an initial contour (either manually or as an output of another segmentation method). Generally, this initial contour is usually somewhat close to the desired final contour, although it may deviate substantially, but still provide the desired result of defining the boundaries of the structure under going segmentation.

The snakes method 420 takes as input the initial contour and the underlying grayscale image (See step 422) and produces a final contour which lies along the edges of desired structures while having a smooth appearance. Once the initial contour is input, radial lines are drawn normal to each vertex of the initial contour in step 424 and the contour is restricted to move only along these radial directions. In an alternate embodiment, the contour is permitted to move along additional lines, while being restricted in another.

A sampling of the image along these radial directions is performed and one-dimensional derivatives of the image are computed along the radial lines. The position of the contour is iteratively adjusted in step 426 to have its contour on this radial line such that the total energy of the contour is minimized. The total energy of the contour is determined in step 428 and is defined by a sum of three terms in equation (1) as follows:

$$E(v)=\Sigma(\alpha\|v_S\|^2+\beta\|v_{SS}\|^2+\lambda g(v)) \quad \text{EQ.(1)}$$

wherein v is the contour, $v_S$ is the first derivative of the contour, $v_{SS}$ is the second derivative of the contour and g is the negative derivative of the input image evaluated along the contour. Alpha, beta, and lambda are weighting parameters for each term respectively.

The term in EQ. (1) beginning with A promotes close tracking of the contour to the edges on the image. The term beginning with β promotes smoothing of the contour and the term beginning with α promotes the contour length to be relatively short. The radial representation of the contour is converted back to a Cartesian coordinate representation and displayed to the user. An illustration of the above process will now be provided.

Figure 24A:
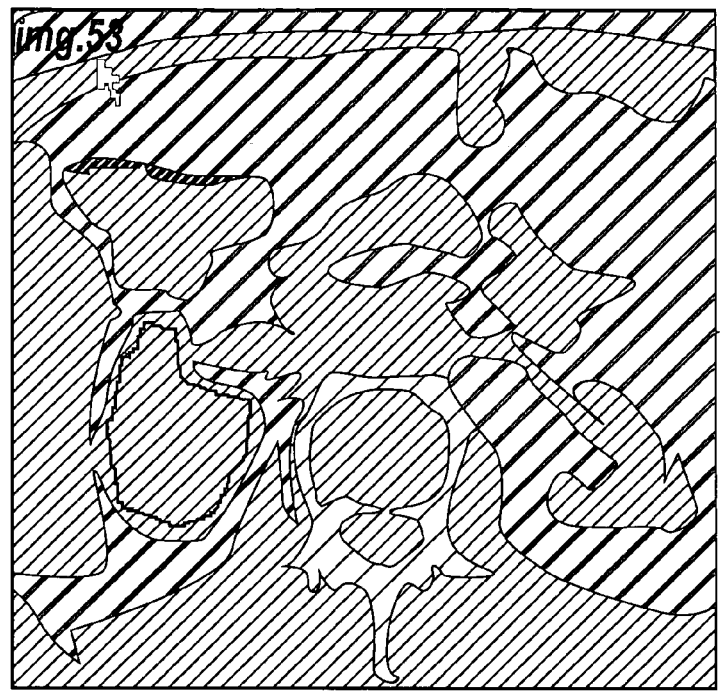
FIGS. 24(A) and 24(B) depict the initial and final contour of a kidney using the snake method.
Figure 24B:
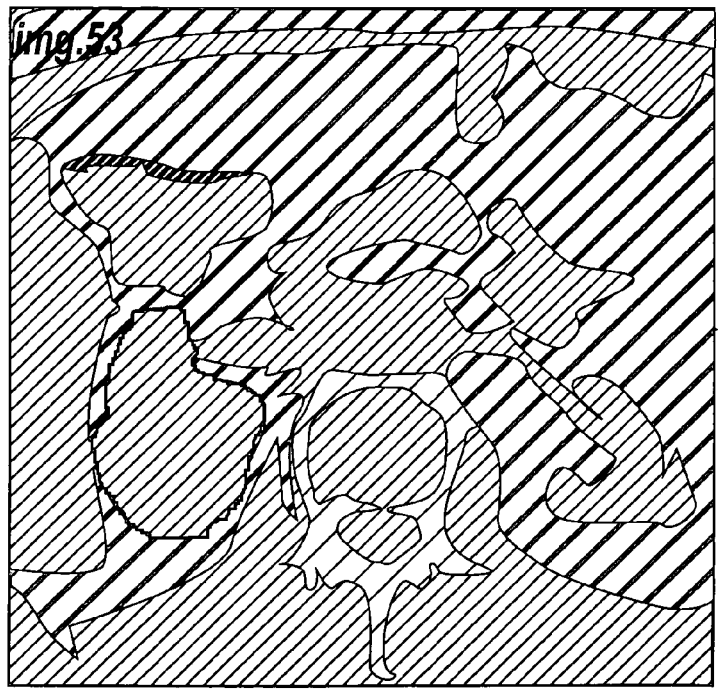
Figure 25A:
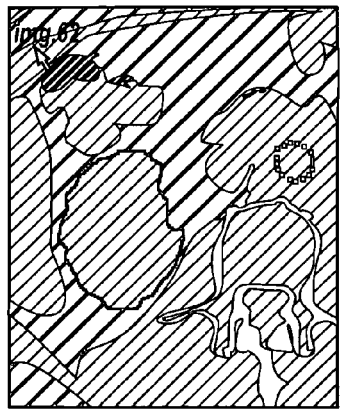
FIGS. 25(A)–25(L) depict a kidney with contouring on 3 slices of 12 outlined using a 2D seed tool of the present invention.
Figure 25B:
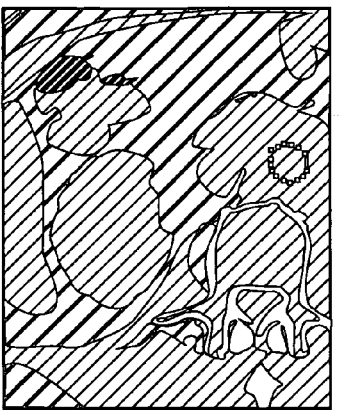
Figure 25C:
Figure 25D:
Figure 25E:
Figure 25F:
Figure 25G:
Figure 25H:
Figure 25I:
Figure 25J:
Figure 25K:
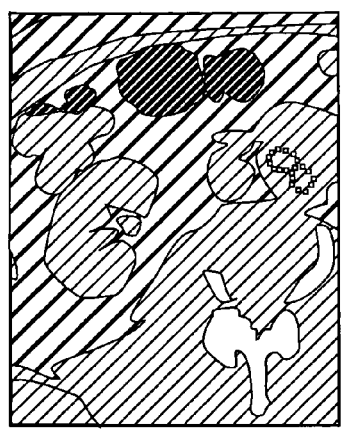
Figure 25L:
Figure 26A:
FIGS. 26(A)–26(L) depict a kidney outlined on all 12 images using a conventional shape-based interpolation tool.
Figure 26B:
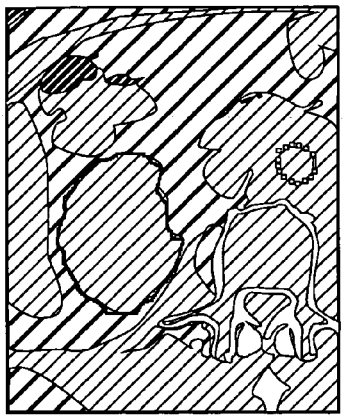
Figure 26C:
Figure 26D:
Figure 26E:
Figure 26F:
Figure 26G:
Figure 26H:
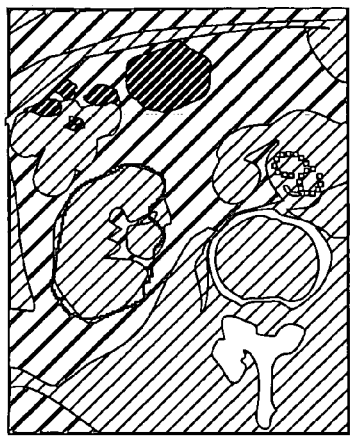
Figure 26I:
Figure 26J:
Figure 26K:
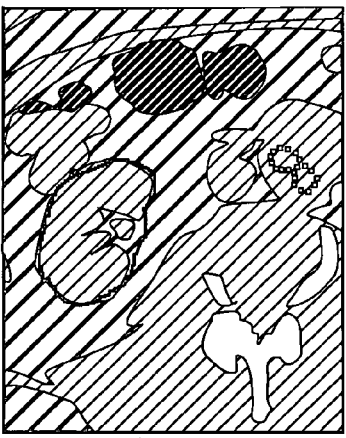
Figure 26L:
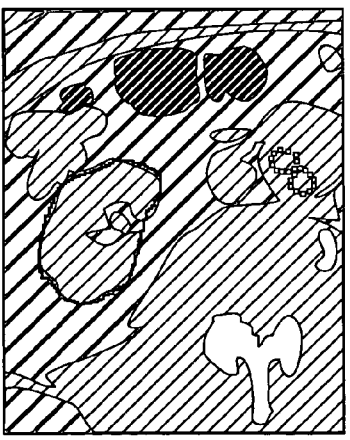
Figure 27A:
FIGS. 27(A)–27(L) depict the resulting corrected image obtained by utilizing the snake method of the present invention.
Figure 27B:
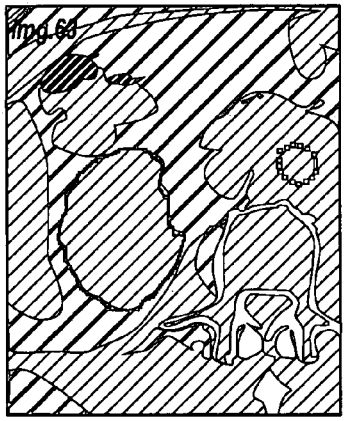
Figure 27C:
Figure 27D:
Figure 27E:
Figure 27F:
Figure 27G:
Figure 27H:
Figure 27I:
Figure 27J:
Figure 27K:
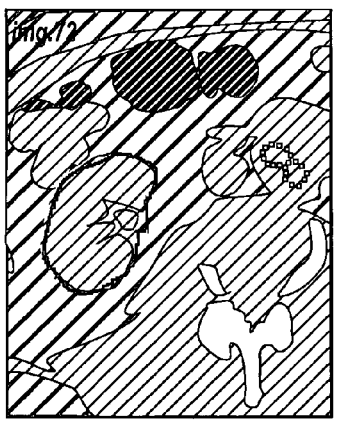
Figure 27L:
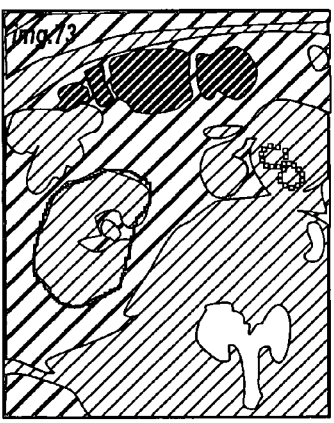

FIG. 24(A) depicts a initial contour for the kidney specified manually by the user. FIG. 24(B) depicts the final contour of the kidney after the application of the snake method. Note that the contour fits the edges of the kidney while remaining smooth.

Combination Tools

The segmentation tools are generally known. However, the segmentation tools may be combined together. The use of the shape based interpolation tool in conjunction with other 2D methods has already been discussed. Here are some other unique scenarios created by the combination of these tools:

An additional aspect of the present invention is the combination of the snakes in conjunction with shape-based interpolation. By combining these aspects of the present invention, 3D structures can be segmented much faster than conventionally, utilizing 2D techniques. The synergy provided by this aspect of the present invention provides a method and system which is very powerful and hence useful in the segmentation of 3D structures in medical images.

The method provides for the utilization of a 2D seedfill, live-wire, or similar method to delineate a structure on multiple images, such as every third image. In the example below, 3 of 9 images have a structure delineated. A shape-based interpolation technique is utilized to obtain approximate delineations on the remaining 6 images. Since the kidney is not a linear varying structure the shape-based interpolation did not perform very well. However, these approximate delineations of the remaining 6 images are then used as initial contours for the Snakes method. The snakes method modifies the contours to fit the boundaries of the desired structure and result in much more accurate delineations on the 6 intermediate images.

FIGS. 25(A)–25(L) depict a kidney with an initial contour on 3 slices of 12 outlined using a 2D seed tool. FIGS. 26(A)–26(L) depict a kidney outlined on all 12 images using a shape-based interpolation tool. FIGS. 27(A)–27(L) depict the resulting corrected image obtained by utilizing the snake method of the present invention.

Another approach is to use the segmentation results from another time point or a baseline scan to provide the initial contours for the current time point. The snake algorithm can then be used to automatically adjust the boundaries to account for the differences in the lesion or tissue that occurred between scans. A variation of this would be for use in template matching segmentation. In template matching a reference image is carefully segmented. Then registration (usually deformable registration) between the reference image and the new test image to be classified is performed. Once the deformation required to transform the reference image to the test image is determined this deformation can be applied to the segmentation overlays to classify the new image. Snakes could then be applied to fine-tune the end results.

Another combination tool is to combine seed fill with multi-channel segmentation. In this scenario the user clicks on a region of interest in one channel of data to initiate seeded region growing. The results of the seeded region growing are then automatically used for the initiation of the multi-channel segmentation. This results in one click multi-channel segmentation.

Quantitative Feature Extraction

After the user is done delineating the different regions and tissue types on the images, they can extract different shape and intensity features associated with the segmentations. These features are displayed on screen and also saved into the database. The following is a list of some of the quantitative features computed by the system:

1) total volume of each labeled region or area of a region in 2D;

2) coordinates of the centroid of each labeled region.

3) coordinates of the bounding cube around the labeled region.

4) row, column, and slice extent of each labeled region.

5) the cross-product diameters of each labeled region (a principal component transform is used to determine these cross-product diameters);

6) coordinates of the end points of the principal axes diameters; and 7) mean, standard deviation, minimum, and maximum image pixel intensities within the labeled region.

Standard Reports

The following are a representative sampling of reports that can be created by the present invention. This list is illustrative only and not limiting to the type of reports that the present invention can produce, as will be appreciated by those skilled in the art.

Volume Report—Volumes of all labeled regions for all image series in the database;

Specific Volume Report—Volumes of all regions with a specific label for all image series in the database;

Area Report—2D Areas of all labeled regions for all images in the database;

Specific Area Report—2D Areas of all regions with a specific label for all images in the database; and Area and Maximal Diameter Report—2D Areas and Maximum Diameters for all labeled regions for all images in the database.

The present invention has many practical uses that persons of ordinary skill in the art will readily appreciate. The implementation of the tools previously described make for a flexible and general-purpose image processing workstation capable of being utilized in a variety of pharmaceutical and patient care applications. Some potential uses for the system include, but are not limited to:

Measurements of tumor volume and tumor cross-sectional diameters from CT and MR images of brain, head, neck, and chest.

Multiple sclerosis (MS) lesion load measurement from MR images of the brain.

Articular cartilage volume and thickness measurement from MR images of the knee.

Delineation of abdominal aortic aneurysm (AAA) from thoracic CT images.

Delineation of brain structures for neuro-degenerative diseases on MR images.

Delineation of prostate from trans-rectal ultrasound images.

Delineation of the heart wall (endocardial and epicardial contours) from cardiac MR images.

Assessment of patients with multiple studies or where quantitative information is needed for proper clinical care.

It will be apparent to those skilled in the art that various modifications and variations can be made in the present invention and in construction of this invention without departing from the scope or intent of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for image registration and quantitative feature extraction from the images, the system comprising:
   an imaging workstation; and
   a database server in communication with the imaging workstation, wherein the imaging workstation includes:
   a data processor with memory capable of inputting and outputting data and instructions to peripheral devices;
   a graphical user interface capable of interfacing with and navigating an imaging software product, wherein the imaging software product is capable of instructing the data processor, the imaging software product comprises:
   instructions to register images;
   instructions to segment images;
   instructions to extract features from images; and
   instructions to store and retrieve one or more registered images, segmented images, quantitative image features and quantitative image data from the database server.

2. The system of claim 1, wherein the software product further includes instructions to perform queries on the database server.

3. The system of claim 1, wherein the software product further comprises instructions to perform multi-modality image registration.

4. The system of claim 1, wherein the software product further includes instructions to perform multi-channel region segmentation.

5. The system of claim 1, wherein the software product further includes instructions to perform shape-based interpolation.

6. The system of claim 1, wherein the quantitative image data further includes serial/longitudinal data.

7. The system of claim 6, wherein the quantitative image data is extracted from 2D and 3D images.

8. The system of claim 1, wherein the quantitative image data is extracted from 2D and 3D images.

9. The system of claim 5, wherein the shaped-based interpolation is modified to perform a regional adjustment of the contour based on the image properties.

10. The system of claim 1, wherein the software product further includes instructions to fuse information from multiple modalities.

11. The system of claim 1, wherein the software product further includes instructions to display segmented images as one of translucent regions and boundaries as an overlay on top of an image.

12. The system of claim 11, wherein the degree of translucency of the regions and boundaries is adjustable.

13. The system of claim 1, that further includes capabilities for generating and storing audit trails.

14. The system of claim 1, wherein the software product further comprises instructions to:
   select an initial contour of a structure in an image set;
   identify each vertex of an initial contour;
   identity radial lines normal to each vertex of the initial contour, wherein the initial contour is restricted to move only along the radial lines;
   sample the image set along the radial lines;
   compute one-dimensional derivatives of the structure along the radial lines; and
   iteratively adjust positioning of the initial contour on the radial line and calculating total energy, wherein the initial contour is adjusted such that the total energy is minimized.

15. The system of claim 14, wherein the total energy is defined by $$E(v)=\Sigma(\alpha\|v_S\|^2+\beta v_{3S}\|^2+\lambda g(v)).$$

16. The system of claim 14, wherein a final radial representation of the contour is convened back to a Cartesian-coordinate for presentation to the user.

17. The system of claim 9, wherein the regional adjustment of the contour based on the local image properties further comprises select an initial contour of a structure in an image set, identify each vertex of an initial contour, identify radial lines normal to each vertex of the initial contour, wherein the initial contour is restricted to move only along the radial lines, sample the image set along the radial lines, compute one-dimensional derivatives of the structure along the radial lines, and iteratively adjust positioning of the initial contour on the radial line and calculating total energy, wherein the initial contour is adjusted such that the total energy is minimized.

18. The system of claim 1, wherein the graphical user interface permits viewing of an arbitrary number of images in a grid by clicking and dragging a grid layout tool that shows a grid layout of the images to be displayed.

19. A computer implemented method for performing a study on image data using an image analysis system having an imaging workstation, a database server in communication with the imaging workstation, wherein the imaging workstation includes a data processor with memory capable of inputting and outputting data and instructions to peripheral devices and a graphical user interface capable of interfacing with and navigating an imaging software product, wherein the imaging software product is capable of instructing the data processor, the method comprising:
   importing one or more image sequences from the database server for a one or more patients involved in the study;

registering the images to align the different image sequences with one of each other and to a baseline image set;

performing segmentation to find one or more objects of interest in the entire image sequence;

performing feature extraction to determine quantitative information about the objects of interest; and storing the objects of interest and the quantitative information about the objects of interest in the database server.

20. The method of claim 19 further comprises performing a regional adjustment of the contour based on the local image characteristics.

21. The method of claim 19, wherein the quantitative image data further includes serial/longitudinal data.

22. The method of claim 21, wherein the quantitative image data is extracted from 2D and 3D images.

23. The method of claim 19, wherein the quantitative image data is extracted from 2D and 3D images.

24. The method of claim 19 further comprising fusing information from multiple modalities.

25. The method of claim 19 further comprising displaying segmented images as one of translucent regions and boundaries as an overlay on top of an image.

26. The method of claim 25 further comprising the ability to vary the translucency of the regions and boundaries between a range or subset of a range from opaque to transparent.

27. The method of claim 20, wherein the regional adjustment further comprising:

selecting an initial contour of a structure in an image set;

identifying each vertex of the initial contour;

identifying radial lines normal to each vertex of the initial contour, wherein the initial contour is restricted to move only along the radial lines;

sampling the image set along the radial lines;

computing one-dimensional derivatives of the structure along the radial lines; and iteratively adjusting positioning of the initial contour on the radial line and calculating total energy, wherein the initial contour is adjusted such that the total energy is minimized.

28. The method of claim 27, wherein the total energy is defined by $$E(v)=\Sigma(\alpha\|v_S\|^2+\beta\|v_{SS}\|^2+\lambda g(v)).$$

29. The method of claim 27, wherein a final radial representation of the contour is converted back to a Cartesian-coordinate for presentation to the user.

30. The method of claim 27, wherein selecting the initial contour comprises one of the following: manual painting, polygon drawing, seed-fill, live-wire, multi-channel segmentation and single channel segmentation.

31. The system of claim 19 further comprising storing audit data associated with the images in the database server.

32. An image analysis system, comprising:

an imaging workstation;

a database server in communication with the imaging workstation;

wherein the imaging workstation includes a data processor with memory capable of inputting and outputting data and instructions to peripheral devices and a graphical user interface capable of interfacing with and navigating an imaging software product, wherein the imaging software product is capable of instructing the data processor, the imaging software product comprises:

instructions to store and retrieve one or more registered images, segmented images, quantitative image features and quantitative image data and from the database server; and instructions to store audit data in the database server that tacks the use and changes of the registered images, the segmented images, the quantitative image features and quantitative image data.

33. A method for segmenting images from a sequence of images, comprising:

performing seeded region growing to generate a segmented region on one or more images and one or more regions of interest, the seeded region growing further comprising identifying a point within a region to be segmented on a particular image and identifying pixels surrounding the point having a similar intensity range; and performing shaped based interpolation that further comprises identifying the segmented region(s) identified during the seeded region growing on the other images in the sequence of images to segment the identified region(s) in all of the sequence of images.

34. A method for segmenting images from a sequence of images, comprising:

determining an initial contour for a segmented region in an image;

performing shaped based interpolation that further comprises identifying the segmented region identified from the image for the other images in the sequence of images to segment the segmented region in all of the sequence of images; and performing snake segmentation on segmented regions in the sequence of images to generate a refined segmented region for the sequence of images, the snake segmentation further comprising selecting an initial contour of a structure in an image set; identifying each vertex of the initial contour; identifying radial lines normal to each vertex of the initial contour, wherein the initial contour is restricted to move only along the radial lines; sampling the image set along the radial lines; computing one-dimensional derivatives of the structure along the radial lines; and iteratively adjusting positioning of the initial contour on the radial line and calculating total energy, wherein the initial contour is adjusted such that the total energy is minimized.

35. The method of claim 34, wherein the total energy is defined by $$E(v)=\Sigma(\alpha\|v_S\|^2+\beta\|v_{SS}\|^2+\lambda g(v)).$$

36. The method of claim 34, wherein a final radial representation of the contour is converted back to a Cartesian-coordinate for presentation to the user.

37. The method of claim 34, wherein determining the initial contour is one of the following: manual painting, polygon drawing, seed-fill, live-wire, multi- or single-channel segmentation.

38. The method of claim 34, wherein the method of identifying the initial contour is from using the contours identified on another image series for the same patient or subject.

39. The method of claim 34, wherein the method of identifying the initial contour is from a template or reference image.

40. A method for segmenting images from a sequence of images, comprising:

generating a segmented image from a reference image;

determining registration between the reference image and a new image to generate a new image segmentation;

performing snake segmentation on the new image segmentation to generate a segmented region within the particular image, the snake segmentation further comprising selecting an initial contour of a structure in an image set; identifying each vertex of the initial contour; identifying radial lines normal to each vertex of the initial contour, wherein the initial contour is restricted to move only along the radial lines; sampling the image set along the radial lines; computing one-dimensional derivatives of the structure along the radial lines; and iteratively adjusting positioning of the initial contour on the radial line and calculating total energy, wherein the initial contour is adjusted such that the total energy is minimized.

41. A method for segmenting images from a sequence of images, comprising:

performing seed region segmentation to generate a segmented region within the particular image, the seed region segmentation further comprising identifying a point within a region to be segmented on a particular image and identifying pixels surrounding the point having a predetermined intensity; and performing multi-channel segmentation in order to segment the segmented region from each image in an image set.

42. A method for segmenting images from a sequence of images, comprising:

determining an initial contour for a segmented region in an image, the initial contour being determined a segmentation tool; and performing snake segmentation on segmented region of the image to generate a refined segmented region for the image, the snake segmentation further comprising selecting an initial contour of a structure in an image set; identifying each vertex of the initial contour; identifying radial lines normal to each vertex of the initial contour, wherein the initial contour is restricted to move only along the radial lines; sampling the image set along the radial lines; computing one-dimensional derivatives of the structure along the radial lines; and iteratively adjusting positioning of the initial contour on the radial line and calculating total energy, wherein the initial contour is adjusted such that the total energy is minimized.

43. The method of claim 42, wherein the total energy is defined by $$E(v) = \Sigma(\alpha \|v_S\|^2 + \beta \|v_{SS}\|^2 + \lambda g(v)).$$

44. The method of claim 43, wherein a final radial representation of the contour is converted back to a Cartesian-coordinate for presentation to the user.

45. The method of claim 42, wherein the segmentation tool comprises one or more of manual painting, polygon drawing, seed-fill, live-wire, multi-channel segmentation and single-channel segmentation.

46. The method of claim 42, wherein the method of identifying the initial contour is from using the contours identified on another image series for the same patient or subject.

47. The method of claim 42, wherein the method of identifying the initial contour is from a template or reference image.

* * * * *